(12) United States Patent
Kowalski et al.

(10) Patent No.: US 8,481,750 B2
(45) Date of Patent: Jul. 9, 2013

(54) DERIVATIVES OF 6,7-DIHYDRO-5H-IMIDAZO[1,2-α]IMIDAZOLE-3-CARBOXYLIC ACID AMIDES

(75) Inventors: Jennifer A. Kowalski, New Milford, CT (US); Matt Aaron Tschantz, Newtown, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/375,768

(22) PCT Filed: May 28, 2010

(86) PCT No.: PCT/US2010/036498
§ 371 (c)(1),
(2), (4) Date: Feb. 7, 2012

(87) PCT Pub. No.: WO2010/141330
PCT Pub. Date: Dec. 9, 2010

(65) Prior Publication Data
US 2012/0178734 A1    Jul. 12, 2012

Related U.S. Application Data

(60) Provisional application No. 61/183,100, filed on Jun. 2, 2009.

(51) Int. Cl.
*A61K 31/4188* (2006.01)
*C07D 401/14* (2006.01)
*C07D 403/12* (2006.01)
*C07D 401/12* (2006.01)
*C07D 487/04* (2006.01)

(52) U.S. Cl.
USPC ............... 548/303.1; 546/273.1; 546/194; 546/256; 544/364; 544/131; 544/238; 544/333; 514/210.18; 514/338; 514/253.09; 514/318; 514/333; 514/233.2; 514/393

(58) Field of Classification Search
USPC ................................. 548/303.1; 546/273.1
See application file for complete search history.

(56) References Cited

U.S. PATENT DOCUMENTS

| | | |
|---|---|---|
| 3,668,217 A | 6/1972 | Fujinami et al. |
| 3,741,981 A | 6/1973 | Fujinami et al. |
| 3,846,441 A | 11/1974 | Mine et al. |
| 4,911,748 A | 3/1990 | Prisbylla |
| 4,944,791 A | 7/1990 | Schroder et al. |
| 4,977,270 A | 12/1990 | Wee |
| 5,208,250 A | 5/1993 | Cetenko et al. |
| 5,306,822 A | 4/1994 | Cetenko et al. |
| 5,334,606 A | 8/1994 | MacLeod |
| 5,464,856 A | 11/1995 | Cetenko et al. |
| 5,750,553 A | 5/1998 | Claussner et al. |
| 6,063,628 A | 5/2000 | Loeb et al. |
| 6,350,763 B1 | 2/2002 | Kelly et al. |
| 6,353,013 B1 | 3/2002 | Kelly et al. |
| 6,355,664 B1 | 3/2002 | Kelly et al. |
| 6,365,615 B1 | 4/2002 | Kelly et al. |
| 6,414,153 B1 | 7/2002 | Kelly et al. |
| 6,492,408 B1 | 12/2002 | Wu et al. |
| 6,689,804 B2 | 2/2004 | Wu et al. |
| 6,844,360 B2 | 1/2005 | Kelly et al. |
| 6,852,748 B1 | 2/2005 | Kelly et al. |
| 7,304,067 B2 | 12/2007 | Kelly et al. |
| 7,345,074 B2 | 3/2008 | Kelly et al. |
| 7,462,637 B2 | 12/2008 | Kelly et al. |
| 7,517,897 B2 | 4/2009 | Eriksson et al. |
| 7,550,494 B2 | 6/2009 | Wu et al. |
| 7,572,921 B2 | 8/2009 | Kim et al. |
| 7,589,114 B2 | 9/2009 | Brunette |
| 7,589,115 B2 | 9/2009 | Kelly et al. |
| 2004/0006011 A1 | 1/2004 | Gour et al. |
| 2006/0025447 A1 | 2/2006 | Wang et al. |
| 2006/0229287 A1 | 10/2006 | Brunette |
| 2011/0022418 A1 | 1/2011 | He et al. |
| 2011/0224188 A1 | 9/2011 | Barbosa et al. |
| 2012/0178734 A1 | 7/2012 | Kowalski et al. |
| 2012/0252817 A1 | 10/2012 | Lemieux et al. |

FOREIGN PATENT DOCUMENTS

| | | |
|---|---|---|
| EP | 0091596 A2 | 10/1983 |
| EP | 0343643 A2 | 11/1989 |
| EP | 0545478 A1 | 6/1993 |
| JP | 63270665 | 11/1988 |
| JP | 63270667 A | 11/1988 |
| JP | 04273877 A | 9/1992 |
| JP | 5188631 A | 7/1993 |
| WO | 9518794 A1 | 7/1995 |
| WO | 9839303 A1 | 9/1998 |
| WO | 9911258 A1 | 3/1999 |
| WO | 9949856 A2 | 10/1999 |
| WO | 0107440 A1 | 2/2001 |
| WO | 0130781 A2 | 5/2001 |

(Continued)

OTHER PUBLICATIONS

Golub et al., Science, vol. 286, Oct. 15, 1999, pp. 531-537.*
International Search Report, Form PCT/ISA/210, and Written Opinion, Form PCT/ISA/237, for corresponding PCT/US2010/036498; date of mailing: Aug. 4, 2010.
Takayama, et al; "Quantitative Structure-activity Relationships of Antifungal 1-(3,5-Dichlorophenyl)-2,5-pyrrolidinediones and 3-(3,5-Diochlorophenyl)-2,4-oxazolidinediones"; Agric. Biol. Chem. 1982, 46, 2755-8.
Halim, et al; "3-[2-(3,5-Dimethylpyrazolyl)} Succinic Anhydride: Synthone for the Synthesis of Some Heterocycles with Potential Pharmaceutical Activity"; Monatshefte fuer Chemie, 1994, 125 1437-1442.
Musza, L. L., et al, "Potent New Cell Adhesion Inhibitory Compounds from the Root of *Trichilia rubra*"; Tetrahedron, 1994, 50, 11369-11378.
Boschelli, D. H., et al; "3-Alkoxybenzo[b]thiophene-2-carboxamides as Inhibitors of Neutrophil-Endothelial Cell Adhesion"; J. Med. Chem, 1994., 37, 717.

(Continued)

*Primary Examiner* — Laura L. Stockton
(74) *Attorney, Agent, or Firm* — Michael P. Morris; Philip I. Datlow

(57) ABSTRACT

Derivatives of 6,7-dihydro-5H-imidazo[1,2-a]imidazole-3-carboxylic acid amide exhibit good inhibitory effect upon the interaction of CAMs and Leukointegrins and are thus useful in the treatment of inflammatory disease.

12 Claims, No Drawings

FOREIGN PATENT DOCUMENTS

| WO | 2004/041827 A2 | 5/2004 |
|---|---|---|
| WO | 2004041273 A1 | 5/2004 |
| WO | 2009/070485 A1 | 6/2009 |

OTHER PUBLICATIONS

Boschelli, D. H., et al; "Inhibition of E-Selectin-, ICAM-1-, and VCAM-1-Mediated Cell Adhesion by Benzo[b] thiophene-, Benzofuran-, Indole-, and Naphthalene-2-carboxamides: Identification of PD 144795 as an Antiinflammatory Agent"; J. Med. Chem., 1995, 38, 4597-4614.

Sanfilippo, P. J., et al; "Novel Thiazole Based Heterocycles as Inhibitors of LFA-1/ICAM-1 Mediated Cell Adhesion"; J. Med. Chem. 1995, 38, 1057-1059.

Makagiansar et al., Inhibition of LFA-1/ICAM-1 and VLA-4/VCAM-1 as a Therapeutic Approach to Inflammation and Autoimmune Diseases, Medicinal Research Reviews, vol. 22, No. 2, 146-167, 2002.

Tanaka et al., Potential Immunosuppressive and Antiinflammatory Activities of Malaysian Medicinal Plants Characterized by Reduced Cell Surface Expression of Cell Adhesion Molecules, Phytotherapy Research, 15, pp. 681-686 (2001).

Anderson et al., Targeting ICAM-1/LFA-1 interaction for controlling autoimmune diseases: designing peptide and small molecule inhibitors, Peptides, 24, pp. 487-501,2003.

Bremner et al.. Therapy of Crohn's Disease in childhood, Expert Opinion Pharmacother. 3(7). pp. 809-825.2002.

Robinson et al., Medical Therapy of Inflammatory Bowel Disease for the 21st Century. Eur. J. Surg. Suppl 582: 90-98. 1998.

Singh et al., Immune Therapy in inflammatory bowel disease and models of colitis, British Journal of Surgery, 88, 1558-1569, 2001.

Wachlin et al., IL-1beta, IFN-1gamma and TNF-alpha increase vulnerability of pancreatic beta cells to autoimmune destruction, Journal of Autoimmunity, 20, pp. 303-312, 2003.

Elgert, Autoimmunity, Immunology: Understanding the Immune System, pp. 315-330, 1996.

Beers et al., Crohn's Disease; Ulcerative Colitis; Psoriasis; Adult respiratory distress syndrome, The Merck Manual of Diagnosis and Therapy, Seventeenth Edition (online), 1999.

Springer, et al., Adhesion receptors of the immune system; Nature; 1990; vol. 346; pp. 425-434.

Kishimoto et al; Integrins, ICAMs, and Selectins: Role and Regulation of Adhesion Molecules in Neutrophil Recruitment to Inflammatory Sites; Advances in Pharmacology; 1994; vol. 25; pp. 117-138.

Diamond, MS., The dynamic regulation of integrin adhesiveness; Current Biology; 1994; vol. 4; No. 6; pp. 506-517.

Anderson et al., Leukocyte LFA-1, p150,95 Deficiency Syndrome: Functional and Biosynthetic Studies of Three Kinds 1,2, Fed. Proc. 1985, 44, pp. 2671-2677.

Anderson et al., The Severe and Moderate Phenotypes of Heritable Mac-1, LFA-1 Deficiency: Their Quantitative Definition and Relation to Leukocyte Dysfunction and Clinical Features, J. Infect. Dis. 1985, 152, pp. 668-689.

Gorski et al., The role of cell adhesion molecules in immunopathology; Immunology Today; 1994; vol. 15; pp. 251-255.

Rothlein et al; Leukocyte Adhesion in Inflammation: From Discovery to the Clinic; Adhesion Molecules; Wegner, C. D., ed.; 1994; pp. 1-8.

Cosimi et al., In Vivo Effects of Monoclonal Antibody to ICAM-1 (CD54) in Nonhuman Primates With Renal Allografts 1; Journal of Immunology; 1990; vol. 144; pp. 4604-4612.

Kavanaugh et al., Ugh, et al; Treatment of Refractory Rheumatoid Arthritis with a Monoclonal Antibody to Intercellular Adhesion Molecule 1; Arthritis & Rheumatism; Jul. 1994; vol. 37; No. 7; pp. 992-1004.

LeMauff et al., Effect of Anti-LFA1 (CD11a) Monoclonal Antibodies in Acute Regection inHuman Kidney Transplantation, Transplantation, Aug. 1991, 52, pp. 291-295.

Becker et al., Soluble Intercellular Adhesion Molecule-1 Inhibits MHC-Restricted Specific T Cell/Tumor Interation; The Journal of Immunol. Dec. 1993, 151, pp. 7224-7232.

Roep et al., Soluble forms of intercellular adhesion molecule-I in insulin-dependent diabetes mellitus; The Lancet, 1994, 343, pp. 1590-1593.

English translation of JP63270667, 1988.

Patent Abstract of Japan; Publication No. 63270665; Publication Date: Aug. 11, 1998; Applicant: Wakamoto Pharmacuet Co. Ltd.

Wu, et al; Second-Generation Lymphocyte Function-Associated Antigen-I Inhibitors: 1H-Imidazo[1,2-a] imidazol-2-one Derivatives; Journal of Medicinal Chemistry, American Chemical Society, Washington, US; vol. 47; Sep. 29, 2004; pp. 5356-5366.

Patent Abstract of Japan; Publication No. 4273877; Publication Date: Sep. 30, 1992; Applicant: Sumitomo Pharma.

Patent Abstract of Japan; Publication No. 5188631; Publication Date: Jul. 30, 1993; Applicant: Mita Industrial Co. Ltd.

Toyofuku et al., CA 111:7403, 1989.

* cited by examiner

DERIVATIVES OF 6,7-DIHYDRO-5H-IMIDAZO[1,2-α]IMIDAZOLE-3-CARBOXYLIC ACID AMIDES

BACKGROUND OF THE INVENTION

1. Technical Field

The present invention relates generally to a series of novel derivatives of 6,7-dihydro-5H-imidazo[1,2-a]imidazole-3-carboxylic acid amides, the synthesis of these compounds their use in the treatment of inflammatory disease and pharmaceutical compositions comprising these compounds.

2. Background Information

Research spanning the last decade has helped to elucidate the molecular events attending cell-cell interactions in the body, especially those events involved in the movement and activation of cells in the immune system (see generally, von Andrian U H, et al. *N Engl J Med* 2000; 343(14):1020-1034). Cell surface proteins, and especially the Intercellular Cellular Adhesion Molecules ("ICAMs") and "Leukointegrins", including LFA-1, MAC-1 and p150,95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently accepted that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2 or ICAM-3 which are expressed on blood vessel endothelial cell surfaces and on other leukocytes. The interaction of the ICAMs with the Leukointegrins is a vital step in the normal functioning of the immune system Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology*, 1994, 4, 506-532.

A group of individuals has been identified which lack the appropriate expression of Leukointegrins, a condition termed "Leukocyte Adhesion Deficiency I" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it was believed that antagonism of CD18/CD11/ICAM interactions will also inhibit an inflammatory response. The role of LFA-1 in immune cell trafficking and activation is well established and supported by studies with LFA-1 deficient mice and blocking anti-LFA-1 antibodies. In vitro, LFA-1 deficient lymphocytes are characterized by defects in aggregation and proliferation. In vivo parallel deficits in delayed type hypersensitivity (DTH) responses are observed. In animal models of organ transplantation, anti-LFA-1 antibodies have shown efficacy. Taken together these studies provide support for the role of LFA-1 in initiating and/or propagating inflammatory responses (Giblin, P. A. et al. *Curr. Pharm. Design,* 2006, 12: 2771-2795).

It has been demonstrated that the antagonism of the interaction between the ICAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to ICAMs or Leukointegrins include antigen or mitogen-induced lymphocyte proliferation, homotypic aggregation of lymphocytes, T-cell mediated cytolysis and antigen-specific induced tolerance. The relevance of the in vitro studies is supported by in vivo studies with antibodies directed against ICAM-1 or LFA-1. In numerous models of transplant, including cardiac, bowel, islet and cornea, prolongation of graft survival was observed following treatment with anti-LFA-1, alone or in combination anti-ICAM-1 (see for example Nakakura E K et al., *Transplantation* 1993; 55(2):412-417). Anti-LFA-1 antibodies have also shown benefit in animal models of multiple sclerosis, lupus and inflammatory arthritis (see for example Kobayashi Y et al., *Cell Immunol* 1995; 164(2): 295-305). The first LFA-1-targeted therapeutics to be tested clinically were anti-LFA-1 antibodies. Odulimomab showed efficacy in clinical trials of bone marrow transplant (Stoppa A M et al., *Transpl Int* 1991; 4(1):3-7) and in kidney transplant clinical trials (Hourmant M et al. *Transplantation* 1994; 58(3):377-380). The humanized anti-LFA-1 antibody Raptiva® (anti-CD11a, hu1124, efalizumab), marketed for psoriasis has provided the clinical proof of concept for the role of LFA-1 (Leonardi C L et al., *J Am Acad Dermatol* 2005; 52(3 Pt 1):425-433).

Thus, the prior art has demonstrated that large protein molecules which antagonize the binding of the ICAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the ICAMs to the Leukointegrins would make preferable therapeutic agents.

Several small molecules have been described in the literature that affect the interaction of ICAMs and Leukointegrins. For example, U.S. Pat. No. 6,355,664 (and the corresponding WO 98/39303), 6,710,664, 6,977,267, 7,199,125 and WO 2006065908 disclose a class of small molecules, having a hydantoin core, that are inhibitors of the interaction of LFA-1 and ICAM-1. U.S. Pat. No. 6,492,408 (and corresponding WO 01/07440 A1), U.S. Pat. No. 6,844,360, U.S. Pat. No. 6,852,748, U.S. Pat. No. 7,517,897 and US Patent Application Publication 2006/0229287 all disclose compounds having this same activity that instead have a 6,7-dihydro-5H-imidazo[1,2-a]imidazole core and inhibitors with a 1H-imidazo-[1,2-a]imidazol-2-one core are discloses by J-P Wu, et al., *J. Med Chem.* 2004; 47(22) 5356-5366. In addition, U.S. Pat. Nos. 6,673,825 and 6,974,815 and US Patent Application Publication 20060052434 disclose small molecules having a urazole, hexahydrobenzimidazole and pyrrolizine core respectively that are inhibitors of the interaction of LFA-1 and ICAM-1.

BRIEF SUMMARY OF THE INVENTION

The invention comprises a novel class of derivatives of 6,7-dihydro-5H-imidazo[1,2-a]imidazole-3-carboxylic acid amides and methods for making the same. These compounds are useful for the treatment of inflammatory conditions in that they exhibit good inhibitory effect upon the interaction of ICAMs and Leukointegrins. They are also expected to have an improved metabolic profile over known LFA-1 antagonists while maintaining good functional LFA-1 antagonism in a whole blood environment. Thus, the invention further comprises the use of these compounds for the treatment of inflammatory conditions and pharmaceutical compositions comprising the same as active ingredients.

DETAILED DESCRIPTION OF THE INVENTION

In an embodiment, there is provided a compound of formula I

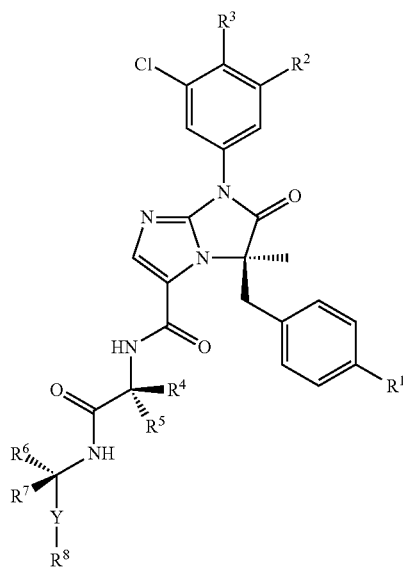

I wherein:
$R^1$ is selected from —CN, —OCF$_3$, halogen, heteroaryl optionally substituted with halogen or $C_{1-3}$alkyl and phenyl optionally substituted with halogen;
$R^2$ is halogen or —CF$_3$;
$R^3$ is H or halogen;
$R^4$ is selected from:
(A) H,
(B) $C_{1-3}$alkyl optionally substituted with one or two groups selected from:
  a) $C_{3-6}$cycloalkyl
  b) —OR$^{11}$,
  c) —NR$^{11}$R$^{12}$,
  d) —SOR$^{11}$,
  e) —SO$_2$R$^{11}$,
  f) —C(O)NR$^{11}$R$^{12}$,
  g) heteroaryl,
  h) heterocyclyl, and
  i) phenyl,
(C) $C_{3-6}$cycloalkyl,
(D) heteroaryl, and
(E) phenyl, optionally substituted with halogen, —OR$^{11}$, —CN or —CF$_3$;
$R^5$ is H, $C_{1-5}$alkyl or $C_{3-4}$cycloalkyl, wherein the $C_{1-5}$alkyl is optionally substituted with —OH; or
$R^4$ and $R^5$, together with the carbon they are bonded to, form a saturated hydrocarbon ring of 3 to 7 carbon atoms, wherein one carbon atom of said hydrocarbon ring:
a) may be optionally substituted with $C_{1-3}$alkyl, halogen, —OR$^{11}$, —CH$_2$OR$^{11}$, —C(O)R$^{11}$, —SO$_2$R$^{11}$, —C(O)CH$_2$CO$_2$R$^{11}$, —NR$^{11}$R$^{12}$, —C(O)NR$^{11}$R$^{12}$, —CN, —C(O)OR$^{11}$, —N(R$^{11}$)C(O)R$^{12}$, heterocyclyl or heteroaryl, wherein said heterocyclyl and heteroaryl are optionally substituted with $C_{1-4}$alkyl, —OH or —CF$_3$,
or
b) may be replaced by —O—, —S—, —S(O)—, —SO$_2$—, —NR$^{11}$—, or —NC(O)R$^{11}$—;
$R^6$ is H or $C_{1-3}$alkyl;
$R^7$ is CH$_3$; or
$R^6$ and $R^7$, together with the carbon they are bonded to, form a saturated hydrocarbon ring of 3 to 7 carbon atoms;
Y is an aromatic 5-8 membered monocyclic group or an aromatic 8-11 membered bicyclic group, each containing 1-4 heteroatoms selected from as N, O, and S;
$R^8$ is
(A) —C(O)NR$^9$R$^{10}$ or
(B) —COOR$^{11}$;
$R^9$ is selected from:
(A) H,
(B) $C_{1-4}$alkyl optionally substituted with one or two groups selected from:
  a) $C_{3-6}$cycloalkyl,
  b) —OR$^{11}$,
  c) —COOR$^{11}$,
  d) —NR$^{11}$R$^{12}$,
  e) —CONR$^{11}$R$^{12}$,
  f) —NR$^{11}$C(O)R$^{12}$,
  g) heteroaryl,
  h) heterocyclyl,
  i) phenyl,
  j) —SOR$^{11}$, and
  k) —SO$_2$R$^{11}$, and
(C) $C_{3-6}$cycloalkyl;
$R^{10}$ is H or $C_{1-3}$alkyl; or
$R^9$ and $R^{10}$ constitute a saturated hydrocarbon bridge of 3 to 6 carbon atoms which together with the N they are bonded to form a heterocyclic ring, and wherein:
a) one or two carbon atoms in said heterocyclic ring are mono or disubstituted with —OR$^{11}$, —CH$_2$OR$^{11}$, —C(O)NR$^{11}$R$^{12}$, —NR$^{11}$C(O)R$^{12}$ and —NR$^{11}$R$^{12}$
or
b) one carbon atom in said heterocyclic ring is optionally replaced by —O—, —S—, —S(O)—, —SO$_2$—, —NR$^{11}$—, —NC(O)R$^{11}$— or —NSO$_2$R$^{13}$—;
$R^{11}$ is H or $C_{1-3}$ alkyl;
$R^{12}$ is H or $C_{1-3}$alkyl; or
$R^{11}$ and $R^{12}$ constitute a saturated hydrocarbon bridge of 3 to 5 carbon atoms which together with the N they are bonded to form a heterocyclic ring, and wherein one carbon atom in said heterocyclic ring may be optionally replaced by —O—, —S—, —S(O)—, —SO$_2$—, —NR$^{13}$—, or —NC(O)R$^{13}$—; and
$R^{13}$ is $C_{1-3}$alkyl;
or a pharmaceutically acceptable salt thereof.

In another embodiment, there is provided a compound of formula I, wherein:
$R^1$ is selected from —CN and —OCF$_3$;
$R^2$ is Cl;
$R^3$ is H or F;
$R^4$ and $R^5$, together with the carbon they are bonded to, form a saturated hydrocarbon ring of 3 carbon atoms;
$R^6$ and $R^7$, together with the carbon they are bonded to, form a saturated hydrocarbon ring of 3 carbon atoms;
Y is a 6-membered heteroaryl group containing one to three ring nitrogen atoms;
$R^8$ is
(A) —COOH, or
(B) —C(O)NR$^9$R$^{10}$;
$R^9$ is selected from:
(A) H,
(B) C$_{1-4}$alkyl optionally substituted with one or two groups selected from:
   a) C$_{3-6}$cycloalkyl,
   b) —OR$^{11}$,
   c) —COOR$^{11}$,
   d) —NR$^{11}$R$^{12}$,
   e) —CONR$^{11}$R$^{12}$,
   f) —NR$^{11}$C(O)R$^{12}$,
   g) heteroaryl,
   h) heterocyclyl, and
   i) phenyl, and
(C) C$_{3-6}$cycloalkyl;
$R^{10}$ is H or C$_{1-3}$alkyl; or
$R^9$ and $R^{10}$ constitute a saturated hydrocarbon bridge of 3 to 5 carbon atoms which together with the N they are bonded to form a heterocyclic ring, and wherein:
a) one or two carbon atoms in said heterocyclic ring are mono or disubstituted with —OR$^{11}$, —CH$_2$OR$^{11}$, —C(O)NR$^{11}$R$^{12}$, —NR$^{11}$C(O)R$^{12}$ and —NR$^{11}$R$^{12}$,
or
b) one carbon atom in said heterocyclic ring is optionally replaced by —O—, —NR$^{11}$—, —NC(O)R$^{11}$— or —NSO$_2$R$^{13}$—;
$R^{11}$ is H or C$_{1-3}$alkyl;
$R^{12}$ is H or C$_{1-3}$alkyl; and
$R^{13}$ is C$_{1-3}$alkyl;
or a pharmaceutically acceptable salt thereof.

In a further embodiment is a compound of formula I, wherein:
$R^1$ is selected from —CN and —OCF$_3$;
$R^2$ is Cl;
$R^3$ is H or F;
$R^4$ and $R^5$ together with the carbon atom they are bonded to constitute a saturated hydrocarbon ring of 3 carbon atoms;
$R^6$ and $R^7$ together with the carbon atom they are bonded to constitute a saturated hydrocarbon ring of 3 carbon atoms;
Y is a pyridyl group;
$R^8$ is —C(O)NR$^9$R$^{10}$ and is connected to the 4-, 5-, or 6-position of Y;
$R^9$ is selected from
(A) H;
(B) C$_{1-4}$alkyl, optionally substituted with one or two groups selected from:
   a) —OH,
   b) —C(O)NH$_2$,
   c) —NHC(O)CH$_3$,
   d) —COOH,
   e) —OCH$_3$,
   f) pyridyl,
   g) furanyl,
   h) imidazolyl,
   i) phenyl,
   j) cyclopropyl, and
   k) —NR$^{11}$R$^{12}$, and
(C) C$_{3-5}$cycloalkyl;
$R^{10}$ is H, —CH$_3$, or —CH$_2$CH$_3$, or
$R^9$ and $R^{10}$ constitute a saturated hydrocarbon bridge of 3 to 5 carbon atoms which together with the N they are bonded to, form a heterocyclic ring, and wherein:
a) one carbon atom in said heterocyclic ring may be optionally substituted with —OH, —CH$_2$OH, —C(O)NH$_2$, —N(CH$_3$)$_2$, —NHC(O)CH$_3$ or —NCH$_3$C(O)CH$_3$, or
b) wherein one carbon atom in said heterocyclic ring may be optionally replaced by —O—, or —NH—, —NCH$_3$—, —NSO$_2$CH$_3$— or —NC(O)CH$_3$—;
$R^{11}$ is H or —CH$_3$;
$R^{12}$ is H or —CH$_3$;
or a pharmaceutically acceptable salt thereof.

In yet another embodiment is a compound of formula I wherein:
$R^1$ is selected from —CN and —OCF$_3$;
$R^2$ is Cl;
$R^3$ is H or F;
$R^4$ and $R^5$ together with the carbon atom they are bonded to constitute a saturated hydrocarbon ring of 3 carbon atoms;
$R^6$ and $R^7$ together with the carbon atom they are bonded to constitute a saturated hydrocarbon ring of 3 carbon atoms;
Y is

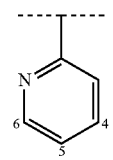

$R^8$ is —C(O)NR$^9$R$^{10}$ and is connected to the 4- or 5-position of Y;
$R^9$ is selected from
(A) H,
(B) C$_{1-4}$alkyl, optionally substituted with one or two of the following:
   a) —OH,
   b) —C(O)NH$_2$,
   c) —NHC(O)CH$_3$,
   d) —COOH,
   e) —OCH$_3$,
   f) pyridyl,
   g) furan-2-yl,
   h) 1-H-imidazol-1-yl,
   i) phenyl,
   j) cyclopropyl,
   k) —N(CH$_3$)$_2$, and
   l) —NH$_2$, and
(C) C$_{3-4}$cycloalkyl;
$R^{10}$ is —H, or —CH$_3$, or
$R^9$ and $R^{10}$ constitute a saturated hydrocarbon bridge of 3 to 5 carbon atoms which together with the N they are bonded to, form a heterocyclic ring, and wherein one carbon atom in said heterocyclic ring may be optionally substituted with —OH, —CH$_2$OH or —C(O)NH$_2$ or may be optionally replaced by —O—;
or a pharmaceutically acceptable salt thereof.

In yet a further embodiment is a compound of formula I, wherein:
R¹ is selected from —CN and —OCF₃;
R² is Cl;
R³ is H or F;
R⁴ and R⁵ together with the carbon atom they are bonded to constitute a saturated hydrocarbon ring of 3 carbon atoms;
R⁶ and R⁷ together with the carbon atom they are bonded to constitute a saturated hydrocarbon ring of 3 carbon atoms;
Y is

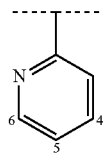

R⁸ is —C(O)NR⁹R¹⁰ and is connected to the 4- or 5-position of Y;
R⁹ is selected from
  (A) H,
  (B) C₁₋₄alkyl, optionally substituted with one of the following:
    a) —OH,
    b) —C(O)NH₂, or
    c) —COOH, and
  (C) cyclopropyl;
R¹⁰ is H;
or a pharmaceutically acceptable salt thereof.

The following are representative compounds of the invention which can be made by the methods described in the general synthetic schemes, the synthetic examples, and known methods in the art.

TABLE 1

TABLE 1-continued
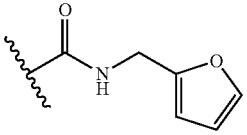 [SMILES: *C(=O)NCc1ccco1]
| Ex | R¹ | R³ | R⁸ 6 | R⁸ 5 | R⁸ 4 |
|---|---|---|---|---|---|
| 3 | CN | H | H | 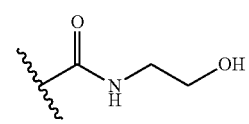 | H |
| 4 | CN | H | H | H | 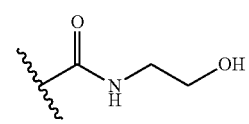 |
| 5 | CN | H | H | 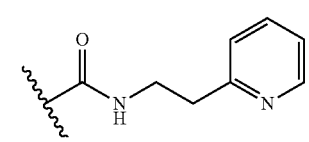 [SMILES: *C(=O)NCCc1ccccn1] | H |
| 6 | CN | H | H | H | 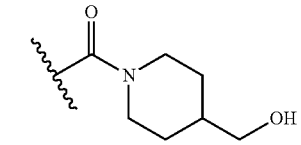 [SMILES: *C(=O)N1CCC(CO)CC1] |
| 7 | CN | H | H | H | 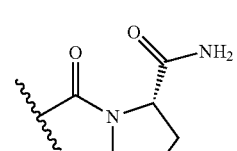 |
| 8 | CN | H | H |  | H |

TABLE 1-continued
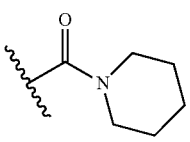 [SMILES: *C(=O)N1CCCCC1]
| Ex | R¹ | R³ | 6 | 5 | 4 |
|---|---|---|---|---|---|
| 9 | CN | H | H | 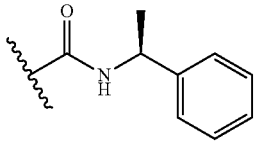 [SMILES: *C(=O)N[C@@H](C)c1ccccc1] | H |
| 10 | CN | H | H | H | 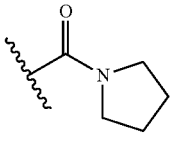 [SMILES: *C(=O)N1CCCC1] |
| 11 | CN | H | 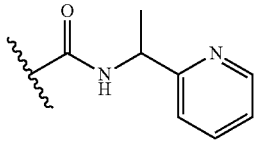 [SMILES: *C(=O)NC(C)c1ccccn1] | H | H |
| 12 | CN | H | 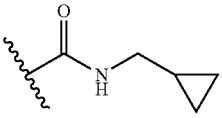 [SMILES: *C(=O)NCC1CC1] | H | H |
| 13 | CN | H | H | 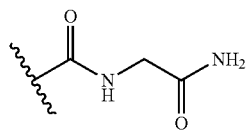 | H |
| 14 | CN | H | H |  | H |

TABLE 1-continued
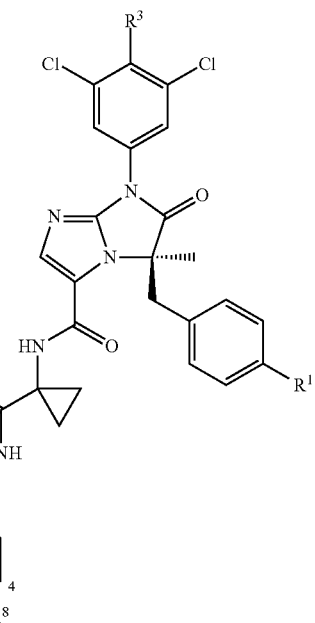
| Ex | R¹ | R³ | R⁸ 6 | R⁸ 5 | R⁸ 4 |
|----|----|----|------|------|------|
| 15 | CN | H | ![acetamidopyrrolidinyl carbonyl] | H | H |
| 16 | CN | H | ![piperidinyl carbonyl] | H | H |
| 17 | CN | H | H | H | ![alaninol amide] |
| 18 | CN | H | ![4-(hydroxymethyl)piperidinyl carbonyl] | H | H |
| 19 | CN | H | H | H | ![aminoethyl amide] |
| 20 | CN | H | ![N-methyl-N-(2-hydroxyethyl) amide] | H | H |

TABLE 1-continued
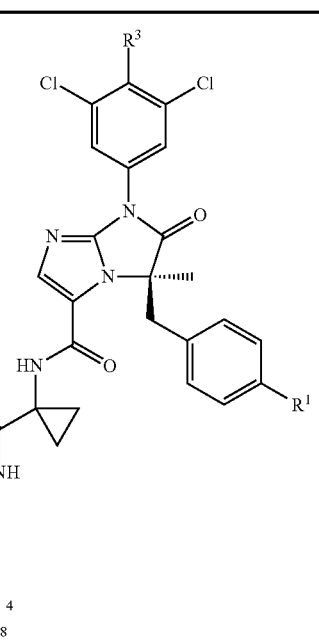
| Ex | R¹ | R³ | 6 | 5 | 4 |
|---|---|---|---|---|---|
| 21 | CN | H | H | (acetamido-N-methylpyridin-3-yl) | H |
| 22 | CN | H | (4-acetylpiperazin-1-yl)carbonyl | H | H |
| 23 | CN | H | (3-carbamoylpiperidin-1-yl)carbonyl | H | H |
| 24 | CN | H | H | H | N-benzylcarbamoyl |
| 25 | CN | H | N-benzylcarbamoyl | H | H |

TABLE 1-continued

| Ex | R¹ | R³ | R⁸ 6 | R⁸ 5 | R⁸ 4 |
|---|---|---|---|---|---|
| 26 | CN | H | ✦C(O)NHCH₂-(4-pyridyl) | H | H |
| 27 | CN | H | H | ✦C(O)NHCH(CH₃)CH₂OH | H |
| 28 | CN | H | ✦C(O)-(2-pyrrolidinyl-C(O)NH₂) | H | H |
| 29 | CN | H | H | ✦C(O)-N(piperidinyl-3-CH₂OH) | H |
| 30 | CN | H | ✦C(O)NHCH₂CH₂OH | H | H |
| 31 | CN | H | H | H | CONHMe |
| 32 | CN | H | H | H | ✦C(O)NHCH₂CH₂-phenyl |

TABLE 1-continued
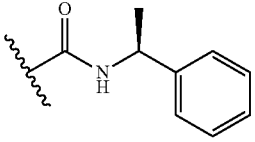 [SMILES: *C(=O)N[C@@H](C)c1ccccc1]
| Ex | R¹ | R³ | R⁸ 6 | R⁸ 5 | R⁸ 4 |
|---|---|---|---|---|---|
| 33 | CN | H | H | 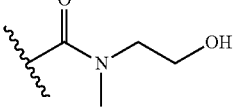 | H |
| 34 | CN | H | H | H | 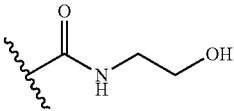 [SMILES: *C(=O)NCCO] |
| 35 | CN | H | H | 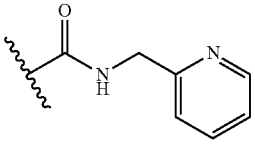 [SMILES: *C(=O)NCc1ccccn1] | H |
| 36 | CN | H | H | 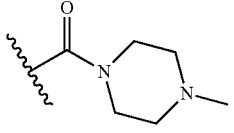 [SMILES: *C(=O)N1CCN(C)CC1] | H |
| 37 | CN | H | H | 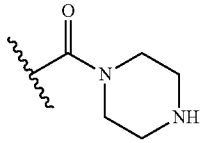 [SMILES: *C(=O)N1CCNCC1] | H |
| 38 | CN | H | H | H | CONMe₂ |
| 39 | CN | H |  | H | H |

TABLE 1-continued

[Structure: central scaffold with R³-substituted 3,5-dichlorophenyl group attached to an imidazo-imidazolone bearing a methyl and 4-R¹-benzyl group, linked via carboxamide to a cyclopropyl-bis-amide terminating in a cyclopropyl-pyridyl group with substituents at positions 4, 5, 6 designated as R⁸.]

| Ex | R¹ | R³ | R⁸ 6 | R⁸ 5 | R⁸ 4 |
|---|---|---|---|---|---|
| 40 | CN | H | ⋎C(O)NH-CH₂CH₂-NH₂ | H | H |
| 41 | CN | H | H | ⋎C(O)NH-CH₂CH₂-OCH₃ | H |
| 42 | CN | H | H | ⋎C(O)-morpholine | H |
| 43 | CN | H | H | H | ⋎C(O)-piperidine-3-C(O)NH₂ |
| 44 | CN | H | H | H | ⋎C(O)-piperidine-2-CH₂OH |

TABLE 1-continued

| Ex | R¹ | R³ | R⁸ 6 | R⁸ 5 | R⁸ 4 |
|---|---|---|---|---|---|
| 45 | CN | H | [pyrrolidine-N-acyl with 3-(N-methyl-N-acetylamino) substituent] | H | H |
| 46 | CN | H | H | [C(O)NH-CH(CH₃)-(4-pyridyl)] | H |
| 47 | CN | H | [C(O)NH-CH(CH₃)-(3-pyridyl)] | H | H |
| 48 | CN | H | [(3S)-3-hydroxypyrrolidine-N-acyl] | H | H |
| 49 | CN | H | H | H | [C(O)NH-CH(CH₃)-CH₂OH] |
| 50 | CN | H | H | [C(O)NH-CH₂-(4-pyridyl)] | H |

TABLE 1-continued

| Ex | R¹ | R³ | R⁸ 6 | R⁸ 5 | R⁸ 4 |
|---|---|---|---|---|---|
| 51 | CN | H | (1-acyl-3-hydroxyazetidine, attached via C=O to N) | H | H |
| 52 | CN | H | H | H | CONH₂ |
| 53 | CN | H | H | H | -C(=O)NH-CH(CH₃)-phenyl (S or R) |
| 54 | CN | H | H | H | (1-acyl-3-acetamidopyrrolidine) |
| 55 | CN | H | H | H | -C(=O)NH-cyclopropyl |
| 56 | CN | H | H | (1-acyl piperazine) | H |

TABLE 1-continued

| Ex | R¹ | R³ | R⁸ 6 | R⁸ 5 | R⁸ 4 |
|----|----|----|------|------|------|
| 57 | CN | H | ~C(O)NH-CH₂CH₂-C(O)NH₂ | H | H |
| 58 | CN | H | H | H | ~C(O)-morpholine (N-linked) |
| 59 | CN | H | H | ~C(O)-N-azetidine-3-OH | H |
| 60 | CN | H | H | H | ~C(O)NH-CH₂-CH(OH)CH₃ |
| 61 | CN | H | H | ~C(O)-N-pyrrolidine-3-N(CH₃)₂ | H |
| 62 | CN | H | H | H | ~C(O)NH-CH₂CH₂-N(CH₃)₂ |

TABLE 1-continued

| Ex | R¹ | R³ | 6 | 5 | 4 |
|---|---|---|---|---|---|
| 63 | CN | H | -C(O)NH-CH₂CH₂-N(CH₃)₂ | H | H |
| 64 | CN | H | H | H | -C(O)NH-CH₂-(4-pyridyl) |
| 65 | CN | H | H | -C(O)NH-CH(CH₃)-phenyl (S) | H |
| 66 | CN | H | H | -C(O)NH-CH(CH₂OH)₂ | H |
| 67 | CN | H | -C(O)-(2-pyrrolidinyl-C(O)NH₂) (S) | H | H |
| 68 | CN | H | -C(O)NH-CH₂CH₂-NH-C(O)CH₃ | H | H |

TABLE 1-continued
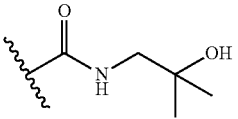 [SMILES: *C(=O)NCC(C)(C)O]
| Ex | R¹ | R³ | R⁸ 6 | R⁸ 5 | R⁸ 4 |
|---|---|---|---|---|---|
| 69 | CN | H | H | H | 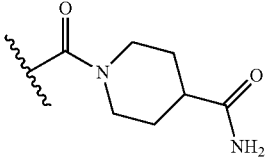 [SMILES: *C(=O)N1CCC(C(N)=O)CC1] |
| 70 | CN | H | H | H | 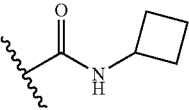 [SMILES: *C(=O)NC1CCC1] |
| 71 | CN | H | H | 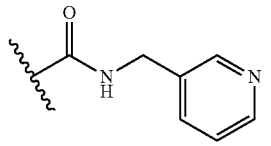 [SMILES: *C(=O)NCc1cccnc1] | H |
| 72 | CN | H | H | H | 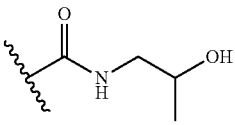 [SMILES: *C(=O)NCC(C)O] |
| 73 | CN | H | H | 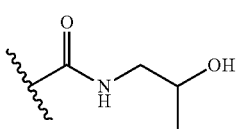 [SMILES: *C(=O)NCC(C)O] | H |
| 74 | CN | H |  | H | H |

TABLE 1-continued

| Ex | R¹ | R³ | R⁸ 6 | R⁸ 5 | R⁸ 4 |
|---|---|---|---|---|---|
| 75 | CN | H | ⸾⸾−C(O)−NH−CH₂CH₂−O−CH₃ | H | H |
| 76 | CN | H | H | H | ⸾⸾−C(O)−NH−CH₂−(2-furyl) |
| 77 | CN | H | H | ⸾⸾−C(O)−NH−CH₂−C(O)OH | H |
| 78 | CN | H | H | ⸾⸾−C(O)−NH−CH₂CH₂−NH₂ | H |
| 79 | CN | H | H | H | ⸾⸾−C(O)−NH−CH₂−(2-pyridyl) |
| 80 | CN | H | H | H | ⸾⸾−C(O)−N(3-hydroxymethylpiperidin-1-yl) |

TABLE 1-continued

[Structure shown: core scaffold with 3,5-dichloro-4-R³ phenyl group attached to imidazo-imidazolone bearing methyl and 4-R¹-benzyl substituents, with carboxamide linker to cyclopropyl-carboxamide-cyclopropyl-pyridine (positions 4, 5, 6 bearing R⁸)]

| Ex | R¹ | R³ | 6 (R⁸) | 5 (R⁸) | 4 (R⁸) |
|---|---|---|---|---|---|
| 81 | CN | H | H | -C(O)NH-CH₂-C₆H₅ (benzyl amide) | H |
| 82 | OCF₃ | F | H | -C(O)NH-cyclopropyl | H |
| 83 | CN | H | -C(O)NH-CH(CH₃)-C(O)NH₂ | H | H |
| 84 | CN | H | H | -C(O)NH-CH₂CH₂-(3-pyridyl) | H |
| 85 | CN | H | H | -C(O)-N(piperidin-1-yl with 4-CH₂OH) | H |
| 86 | CN | H | H | -C(O)NH-C(CH₃)₂-CH₂OH | H |

TABLE 1-continued
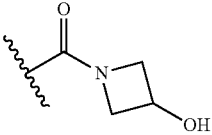 [SMILES: *C(=O)N1CC(O)C1]
| Ex | R¹ | R³ | R⁸ 6 | R⁸ 5 | R⁸ 4 |
|---|---|---|---|---|---|
| 87 | CN | H | H | H | 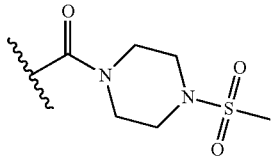 |
| 88 | OCF₃ | F | H | CONH₂ | H |
| 89 | CN | H | H | H | 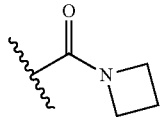 |
| 90 | CN | H | H | 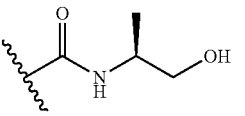 [SMILES: *C(=O)N[C@@H](C)CO] | H |
| 91 | CN | H | H | 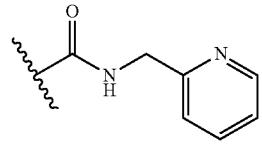 [SMILES: *C(=O)NCc1ccccn1] | H |
| 92 | CN | H | 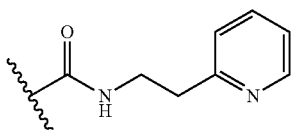 | H | H |
| 93 | CN | H | H |  | H |

TABLE 1-continued
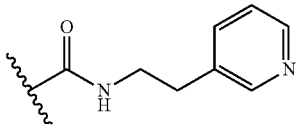 [SMILES: *C(=O)NCCc1cccnc1]
| Ex | R¹ | R³ | R⁸ 6 | R⁸ 5 | R⁸ 4 |
|---|---|---|---|---|---|
| 94 | OCF₃ | H | H | CONH₂ | H |
| 95 | CN | H | H | H | 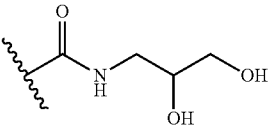 [SMILES: *C(=O)NCC(O)CO] |
| 96 | CN | H | H | H | 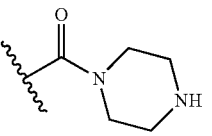 [SMILES: *C(=O)N1CCNCC1] |
| 97 | CN | H | H | H | 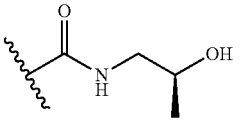 [SMILES: *C(=O)NC[C@H](C)O] |
| 98 | CN | H | CONH₂ | H | H |
| 99 | CN | H | H | 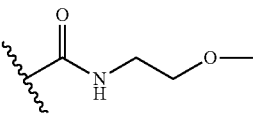 | H |
| 100 | CN | H | H | H |  |

TABLE 1-continued

[Core structure: imidazo-pyrimidinone scaffold with 3,5-dichlorophenyl group bearing R³, methyl-substituted stereocenter with 4-R¹-benzyl group, carboxamide linked to cyclopropyl-carboxamide-cyclopropyl-pyridine (positions 4, 5, 6 with R⁸)]

| Ex  | R¹ | R³ | R⁸ (6) | R⁸ (5) | R⁸ (4) |
|-----|----|----|--------|--------|--------|
| 101 | CN | H  | H | –C(O)–[1-piperidinyl-3-carboxamide] | H |
| 102 | CN | H  | H | –C(O)–NH–CH(CH₃)–C(O)NH₂ (L-alanine amide) | H |
| 103 | CN | H  | H | H | –C(O)–[(3S)-3-hydroxypyrrolidin-1-yl] |
| 104 | CN | H  | –C(O)–[azetidin-1-yl] | H | H |
| 105 | CN | H  | H | H | –C(O)–NH–C(CH₃)₂–CH₂OH |
| 106 | CN | H  | H | –C(O)–NH–CH₂CH₂–N(CH₃)₂ | H |

TABLE 1-continued
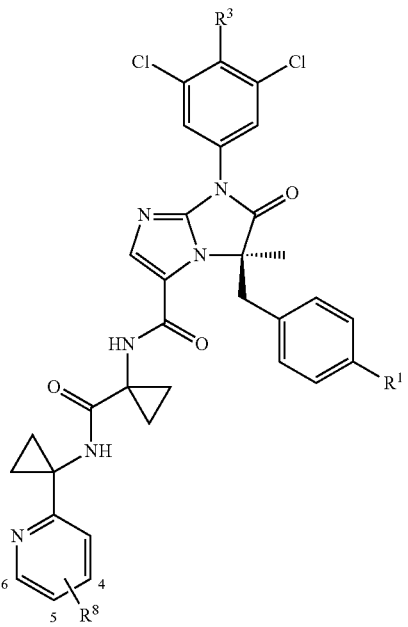
| Ex | R¹ | R³ | R⁸ 6 | R⁸ 5 | R⁸ 4 |
|---|---|---|---|---|---|
| 107 | CN | H | H | H | 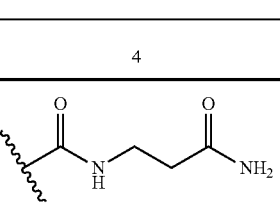 |
| 108 | CN | H | H | H | 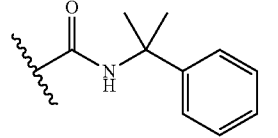 [SMILES: *C(=O)NC(C)(C)c1ccccc1] |
| 109 | CN | H | H | 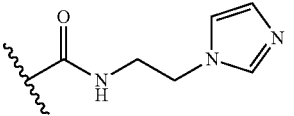 [SMILES: *C(=O)NCCn1ccnc1] | H |
| 110 | CN | H | H | H | 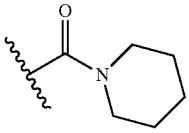 [SMILES: *C(=O)N1CCCCC1] |
| 111 | CN | H | 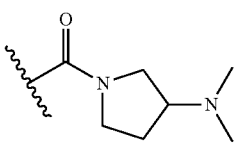 [SMILES: *C(=O)N1CCC(N(C)C)C1] | H | H |
| 112 | CN | H | H | 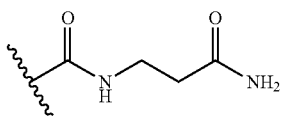 [SMILES: *C(=O)NCCC(N)=O] | H |

TABLE 1-continued

| | | | R[8] | | |
|---|---|---|---|---|---|
| Ex | R[1] | R[3] | 6 | 5 | 4 |
| 113 | CN | H | H | H | acetylpiperazine carbonyl |
| 114 | CN | H | H | H | N-cyclobutyl carboxamide |
| 115 | CN | H | H | H | prolinamide carbonyl |
| 116 | CN | H | H | 3-(N-methylacetamido)pyrrolidine-1-carbonyl | H |
| 117 | CN | H | H | N-(2-hydroxy-2-methylpropyl)carboxamide | H |
| 118 | CN | H | N-((S)-1-phenylethyl)carboxamide | H | H |

TABLE 1-continued
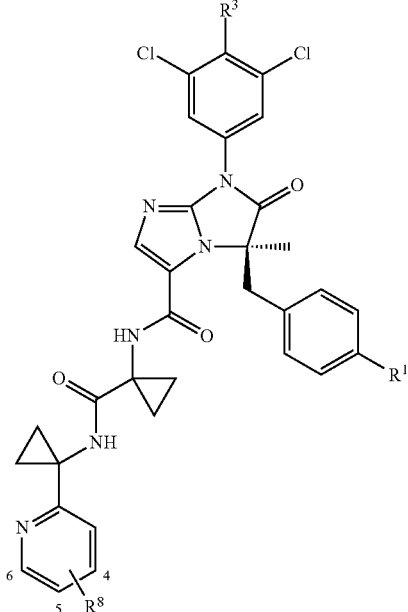
| Ex | R¹ | R³ | R⁸ 6 | R⁸ 5 | R⁸ 4 |
|---|---|---|---|---|---|
| 119 | CN | H | H | 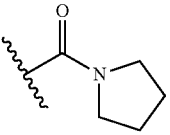 [SMILES: *C(=O)N1CCCC1] | H |
| 120 | CN | H | H | H | 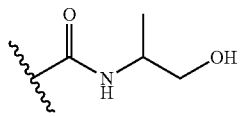 [SMILES: *C(=O)NC(C)CO] |
| 121 | CN | H | H | 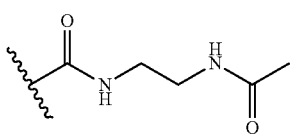 [SMILES: *C(=O)NCCNC(C)=O] | H |
| 122 | CN | H | H | H | 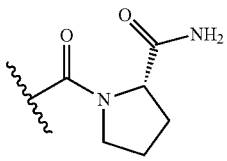 [SMILES: *C(=O)N1CCC[C@H]1C(N)=O] |
| 123 | CN | H | 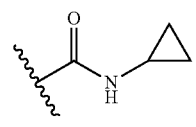 [SMILES: *C(=O)NC1CC1] | H | H |
| 124 | CN | H | H | CONMe$_2$ | H |

TABLE 1-continued

[Structure shown with R³ on dichlorophenyl, R¹ on benzyl group, and pyridine with R⁸ at positions 4, 5, 6]

| Ex | R¹ | R³ | R⁸ 6 | R⁸ 5 | R⁸ 4 |
|---|---|---|---|---|---|
| 125 | CN | H | [2-(hydroxymethyl)piperidin-1-yl]carbonyl | H | H |
| 126 | CN | H | H | C(O)NH-cyclopropyl | H |
| 127 | CN | H | C(O)NHCH₂C(O)NH₂ | H | H |
| 128 | CN | H | H | C(O)NHCH₂CH(OH)CH₃ | H |
| 129 | CN | H | H | H | C(O)NHCH(CH₂OH)₂ |
| 130 | CN | H | H | [(3-hydroxy)pyrrolidin-1-yl]carbonyl | H |

TABLE 1-continued
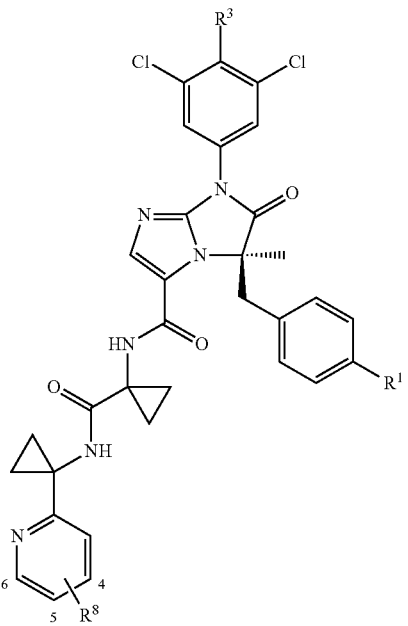
| Ex | R¹ | R³ | R⁸ 6 | R⁸ 5 | R⁸ 4 |
|---|---|---|---|---|---|
| 131 | CN | H | H | H | 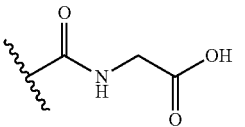 [SMILES: *C(=O)NCC(=O)O] |
| 132 | CN | H | H | H | 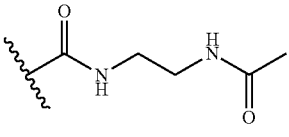 [SMILES: *C(=O)NCCNC(C)=O] |
| 133 | CN | H | H | 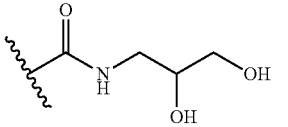 [SMILES: *C(=O)NCC(O)CO] | H |
| 134 | CN | H | H | 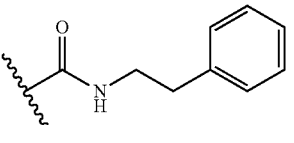 [SMILES: *C(=O)NCCc1ccccc1] | H |
| 135 | CN | H | H | H | 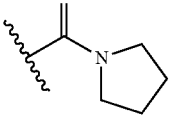 |
| 136 | CN | H | H | H | 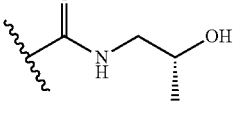 |

TABLE 1-continued
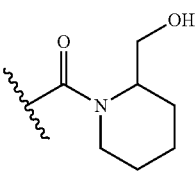 [SMILES: *C(=O)N1CCCCC1CO]
| Ex | R¹ | R³ | R⁸ 6 | R⁸ 5 | R⁸ 4 |
|---|---|---|---|---|---|
| 137 | CN | H | H | 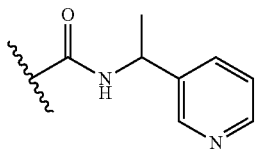 [SMILES: *C(=O)NC(C)c1cccnc1] | H |
| 138 | CN | H | H | H | CONEt₂ |
| 139 | CN | H | H | H | 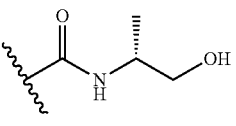 |
| 140 | CN | H | H | CONHMe | H |
| 141 | CN | H | H | 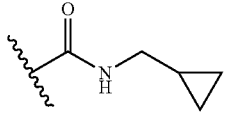 [SMILES: *C(=O)NCC1CC1] | H |
| 142 | CN | H | H | H | 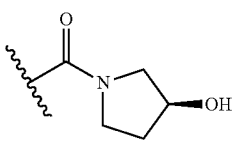 |
| 143 | CN | H |  | H | H |

TABLE 1-continued
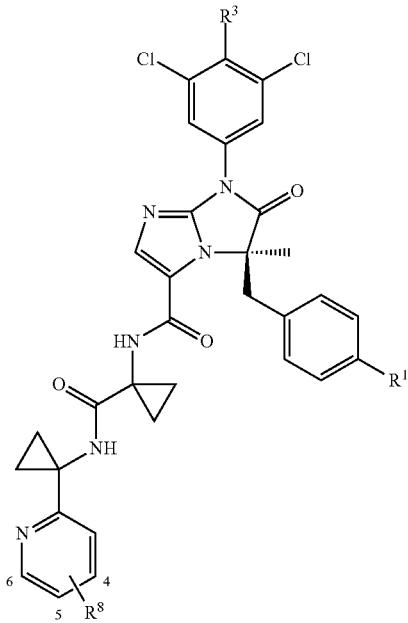
| Ex | R¹ | R³ | R⁸ 6 | R⁸ 5 | R⁸ 4 |
|----|----|----|------|------|------|
| 144 | CN | H | H | H |  |
| 145 | CN | H | 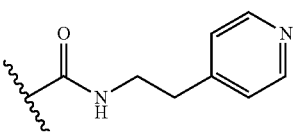 [SMILES: *C(=O)NCCc1ccncc1] | H | H |
| 146 | CN | H | H | H |  |
| 147 | CN | H | H | 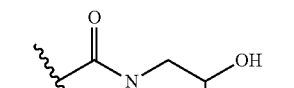 | H |
| 148 | CN | H | H | CONH₂ | H |
| 149 | CN | H | H | H | 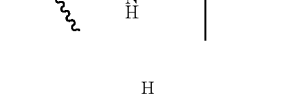 |

TABLE 1-continued
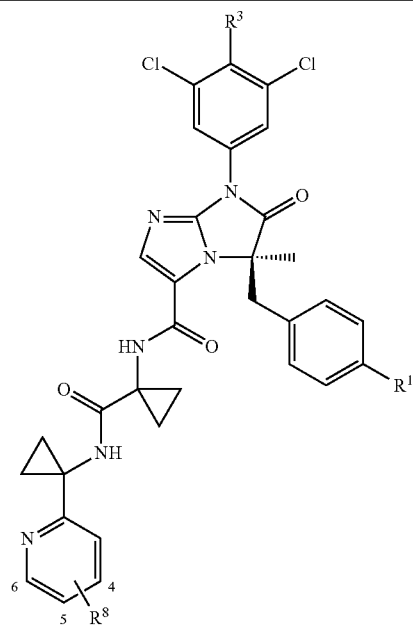
| Ex | R¹ | R³ | R⁸ 6 | R⁸ 5 | R⁸ 4 |
|---|---|---|---|---|---|
| 150 | CN | H | -C(O)NH-CH(CH₃)-CH₂OH | H | H |
| 151 | CN | H | -C(O)NH-CH(CH₃)-(4-pyridyl) | H | H |
| 152 | CN | H | H | -C(O)NH-C(CH₃)₂-phenyl | H |
| 153 | CN | H | H | -C(O)-N(piperazine)-S(O)₂CH₃ | H |
| 154 | CN | H | H | -C(O)-N(CH₃)-CH₂CH₂OH | H |
| 155 | CN | H | H | -C(O)NH-CH(CH₃)-(2-pyridyl) | H |

TABLE 1-continued
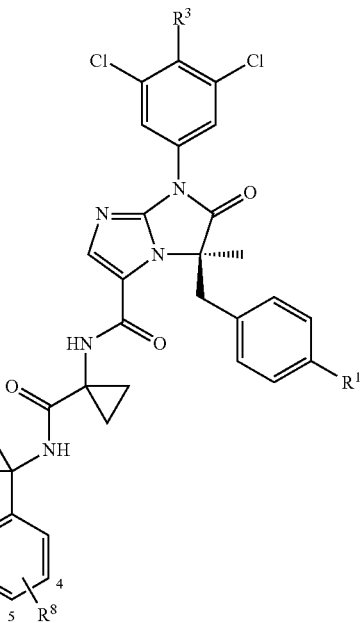
| | | | R⁸ | | |
|---|---|---|---|---|---|
| Ex | R¹ | R³ | 6 | 5 | 4 |
| 156 | CN | H | H | H | *piperazinyl-N-Me carbonyl* |
| 157 | CN | H | *piperazinyl-N-Me carbonyl* | H | H |
| 158 | CN | H | H | *3-acetamidopyrrolidinyl carbonyl* | H |
| 159 | CN | H | H | H | *N-(2-imidazol-1-yl-ethyl)amide* |
| 160 | CN | H | H | *N-(1-pyridin-2-yl-ethyl)amide* | H |
| 161 | CN | H | *3-(hydroxymethyl)piperidinyl carbonyl* | H | H |

TABLE 1-continued
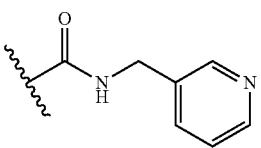 [SMILES: *C(=O)NCc1cccnc1]
| Ex | R¹ | R³ | R⁸ 6 | R⁸ 5 | R⁸ 4 |
|---|---|---|---|---|---|
| 162 | CN | H | 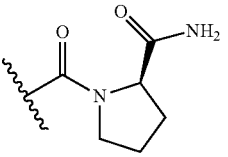 [SMILES: *C(=O)N1CCC[C@@H]1C(N)=O] | H | H |
| 163 | CN | H | H | 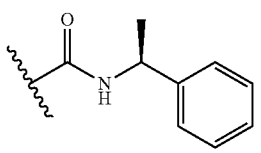 [SMILES: *C(=O)N[C@@H](C)c1ccccc1] | H |
| 164 | CN | F | H | CONH₂ | H |
| 165 | CN | H | 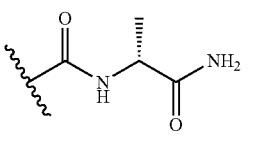 [SMILES: *C(=O)N[C@H](C)C(N)=O] | H | H |
| 166 | CN | H | H | H | 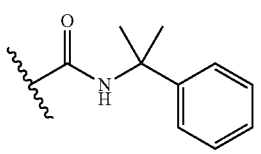 [SMILES: *C(=O)NC(C)(C)c1ccccc1] |
| 167 | CN | H |  | H | H |

TABLE 1-continued
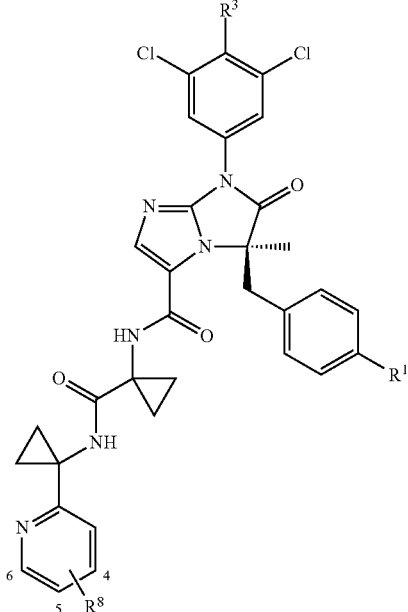
| Ex | R¹ | R³ | R⁸ 6 | R⁸ 5 | R⁸ 4 |
|---|---|---|---|---|---|
| 168 | CN | H | H | H |  |
| 169 | CN | H | H |  | H |
| 170 | CN | H |  | H | H |
| 171 | CN | H | H | 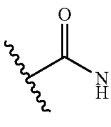 | H |
| 172 | CN | H | H | H |  |

In the table above, an H is shown in the 4-, 5-, or 6-position if $R^8$ is not present in that position.

In another embodiment, the invention relates to a compound selected from compounds 3, 4, 6, 13, 14, 17, 19, 21, 27, 29, 31, 35, 36, 41, 42, 44, 46, 49, 50, 52, 53, 55, 59, 60, 62, 66, 68, 69, 71-73, 77-79, 81, 82, 86-88, 90, 91, 94-96, 99-102, 105, 107, 109, 112, 114, 117, 120, 121, 126, 128, 129, 131-133, 136, 139-142, 144, 146-149, 154, 155, 159, 160, 163, 164, 166 and 172 in Table 1, or the pharmaceutically acceptable salts thereof.

General Synthetic Methods

The compounds of the invention may be prepared by the methods described below. In each of the schemes below, the groups $R^1$-$R^8$ and Y are as defined above for general formula I unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization and/or reverse phase HPLC. HPLC purification methods used anywhere from 0-100% acetonitrile in water containing 0.1% formic acid or 0.1% TFA and used one of the following columns a) Waters Sunfire OBD C18 5 μm 30×150 mm column
b) Waters XBridge OBD C18 5 μm 30×150 mm column
c) Waters ODB C8 5 μm 19×150 mm column
d) Waters Atlantis ODB C18 5 μm 19×50 mm column
e) Waters Atlantis T3 OBD 5 μm 30×100 mm column
f) Phenomenex Gemini Axia C18 5 μm 30×100 mm column Starting materials and reagents are either commercially available or may be prepared by one skilled in the art using methods described in the chemical literature.

Compounds of formula I may be prepared from intermediate II as illustrated in Scheme I. The synthesis of intermediate II is reported by the following U.S. Pat. Nos. 6,492,408, 6,414,161, 6,844,360, and 6,852,748 and also U.S. Application Publications 2006/0025447 and 2007/0173517. The desired $R^1$ on formula II compounds may be obtained by selection of the appropriately substituted reagents as described in Wu et al., U.S. Pat. No. 6,492,408 and Frutos et al., U.S. Pat. No. 6,414,161.

The synthesis of compounds of formula I from intermediate II is illustrated in Scheme I.

Scheme I

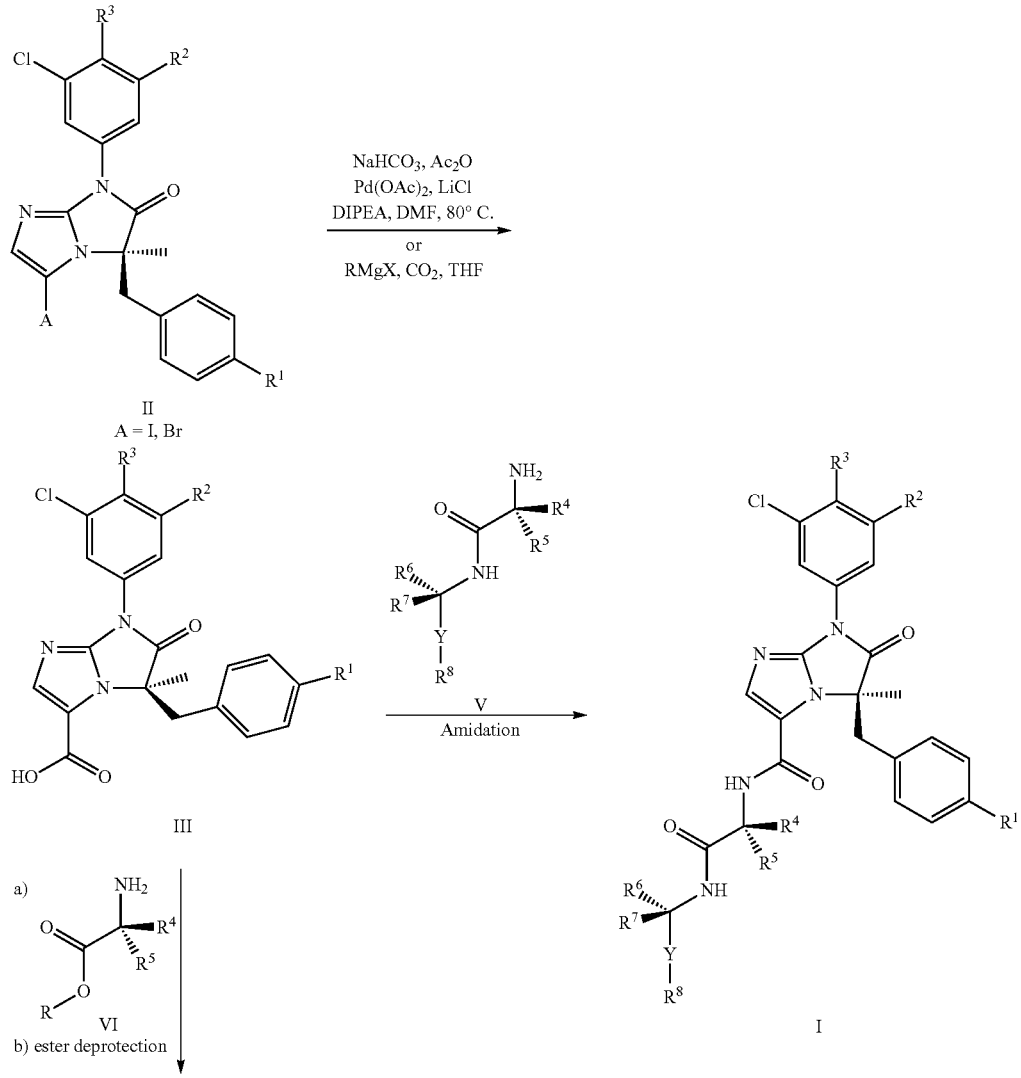

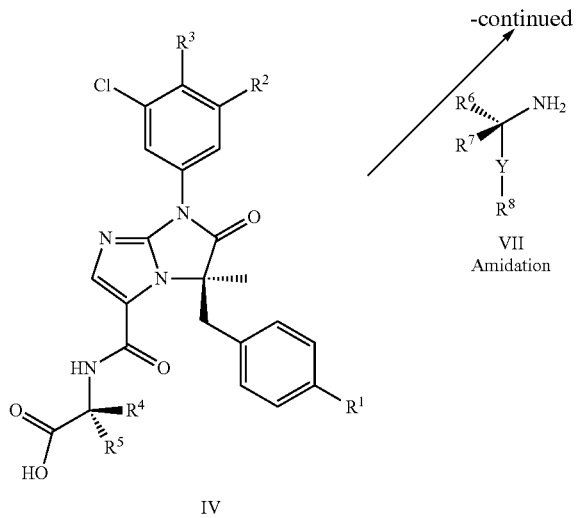

IV

-continued

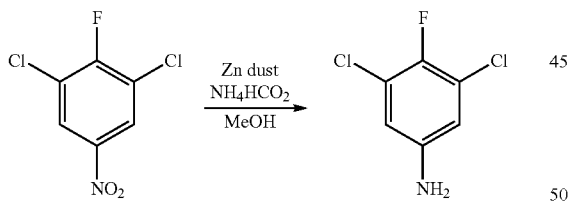

VII
Amidation

As illustrated above, II is transformed into III under Grignard conditions and trapping with $CO_2$ or Pd catalyzed carboxylation. Carboxylic acid III provides I by either amide formation with a suitably functionalized intermediate V or a three step procedure which forms intermediate IV prior to final amide forming reaction. Intermediates V, VI and VII are either commercially available, readily prepared from commercially available starting materials by methods known in the art or disclosed herein. The initial product of formula I may be further modified by methods known in the art to provide additional compounds of the invention. Several examples are provided in the Synthetic Examples section.

Synthesis of Intermediates 3,5-Dichloro-4-fluoro-phenylamine

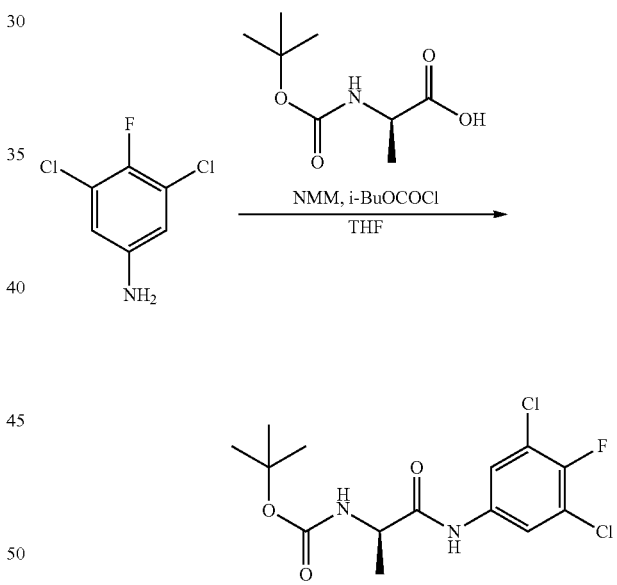

To a solution of 1,3-dichloro-2-fluoro-5-nitro-benzene (71.4 g, 340 mmol) in methanol (1.50 L) was added a solution of ammonium formate (180 g, 2.86 mol) in water (300 mL). Zinc dust (93.4 g, 1.43 mol) was then added in four equal portions over 20 min The reaction was stirred for 1 h and then allowed to cool to room temperature. The reaction mixture was filtered through diatomaceous earth and the filtrate was concentrated in vacuo. Ethyl acetate (300 mL) and water (300 mL) were added and the mixture was again filtered through diatomaceous earth. The layers were separated, and the aqueous layer was further extracted with ethyl acetate (350 mL). The combined organics were washed with 500 mL of brine, dried over $Na_2SO_4$, filtered, and concentrated to afford 56.4 g of the title compound as a brown solid, m/z 180.2 $[M+H]^+$. This material was used without any further purification.

[(R)-1-(3,5-Dichloro-4-fluoro-phenylcarbamoyl)-ethyl]-carbamic acid tert-butyl ester To a cooled (−20° C.) solution of (R)-2-tert-butoxycarbonylamino-propionic acid (57.2 g, 302 mmol) in anhydrous THF (582 mL) was added N-methyl-morpholine (34.9 mL, 317 mmol) at a rate to keep the internal temperature at −15° C. Isobutyl chloroformate (42.0 mL, 317 mmol) was then added over a 20 min period and the resulting mixture was stirred for 30 min. A solution of 3,5-dichloro-4-fluoro-phenylamine (54.4 g, 302 mmol) in THF (160 mL) was then added over 40 min. The reaction mixture was warmed to 20° C. and stirred for 20 h. The reaction mixture was filtered and concentrated in vacuo. To the resulting oil was added MeOH (200 mL) and the solution was concentrated to provide the title compound as a tan colored solid, m/z 295.3 $[M-t-Bu]^+$. This material was used without further purification.

(R)-2-Amino-N-(3,5-dichloro-4-fluoro-phenyl)-propionamide

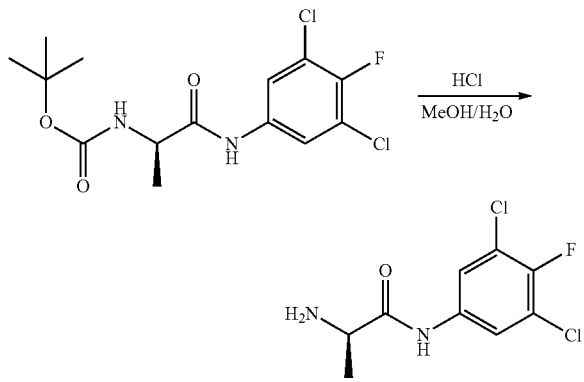

To a solution of hydrochloric acid (12 M, 266 mL, 3.19 mol) in water (272 mL) and MeOH (135 mL) was added a solution of crude [(R)-1-(3,5-dichloro-4-fluoro-phenylcarbamoyl)-ethyl]-carbamic acid tert-butyl ester (208.6 g, max. 594 mmol) in MeOH (600 mL) via an addition funnel over 30 min CH$_2$Cl$_2$ (300 mL) was then added and the reaction mixture was stirred at room temperature overnight. An additional portion of HCl (12M, 100 mL) was added and stirring was continued for another 20 h. The volatile solvents were removed in vacuo and the remaining aqueous mixture was cooled to −15 to −20° C. Toluene (400 mL) was added followed by the addition of NaOH solution (50% aqueous, 300 mL), which was added at a rate to keep the internal temperature below 25° C. The layers were separated and the aqueous layer was extracted with toluene (2×1 L). The combined organic layers were dried with Na$_2$SO$_4$ and concentrated to give 158.3 g of the title compound as a dark brown oil that solidified slowly in the freezer, m/z 251.1 [M+H]$^+$. This crude material was used without further purification.

(2S,5R)-2-tert-Butyl-3-(3,5-dichloro-4-fluoro-phenyl)-5-methyl-1-(2,2,2-trifluoro-acetyl)-imidazolidin-4-one

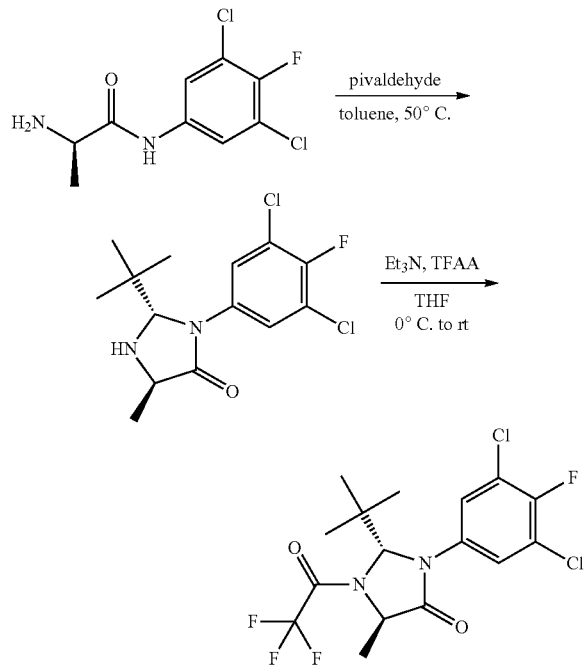

To a solution of (R)-2-amino-N-(3,5-dichloro-4-fluoro-phenyl)-propionamide (149 g crude, max 594 mmol) in toluene (743 mL) at 40° C., was added pivalaldehyde (67.1 mL, 618 mmol) in one portion. The reaction was stirred at 50° C. for 22 h and then all volatiles were removed in vacuo to give a viscous brown oil. Hexane (500 mL) was added and the resulting suspension was stirred at room temperature for 30 min. The mixture was filtered and the solids rinsed with cold hexane. The filtrate was concentrated in vacuo and reprocessed in a similar manner to obtain additional precipitate. The remaining filtrate was diluted with hexane until a black oil separated from the solution. The hexane layer was decanted from this black oil and concentrated in vacuo. The residue was re-dissolved in warm diethyl ether (300 mL) and stored in the freezer for 1.5 h over which time crystal growth was observed. The solids were filtered, and the filtrate reprocessed in a similar manner to obtain additional crystals. All of the collected solids were combined to give 112.2 g of (2S, 5R)-2-tert-butyl-3-(3,5-dichloro-4-fluoro-phenyl)-5-methyl-imidazolidin-4-one as a tan solid. To a solution of this solid in toluene (639 mL) at 0° C. was added triethylamine (73.5 mL, 527 mmol) in one portion. Trifluoroacetic anhydride (58.6 mL, 422 mmol) was added to the reaction mixture over 1 h at a rate to keep the internal temperature below 5° C. The reaction mixture was stirred at 0° C. for 1 h and then warmed to 20° C. over 1 h. The mixture was then cooled to 10° C. and water (1.2 L) was added. The layers were separated and the organic layer was washed with water (1.2 L and then 0.6 L). The combined aqueous layers were extracted with toluene (0.6 L). The combined organic layers were dried over MgSO$_4$ and concentrated in vacuo to give 149.4 g of the title compound as a tan solid, m/z 456.4 [M+MeCN+H]$^+$.

4-[(2R,4R)-2-tert-Butyl-1-(3,5-dichloro-4-fluoro-phenyl)-4-methyl-5-oxo-3-(2,2,2-trifluoro-acetyl)-imidazolidin-4-ylmethyl]-benzonitrile

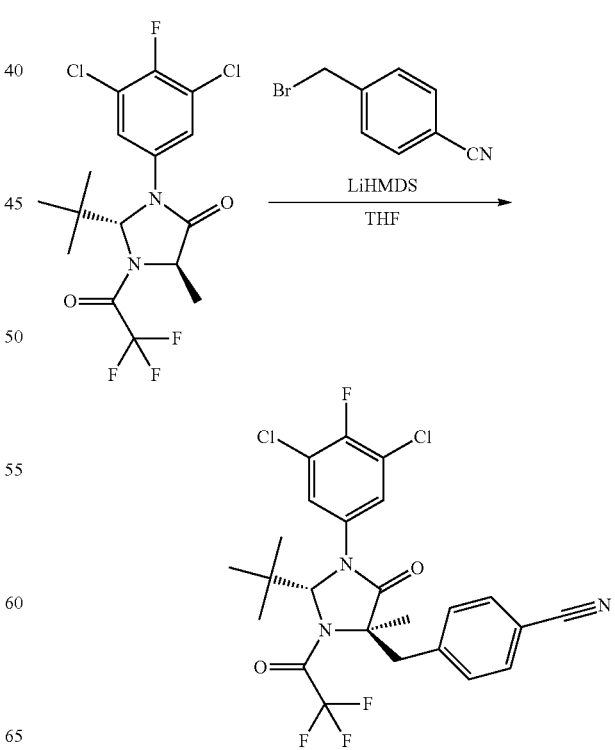

To a solution of (2S,5R)-2-tert-butyl-3-(3,5-dichloro-4-fluoro-phenyl)-5-methyl-1-(2,2,2-trifluoro-acetyl)-imidazolidin-4-one (158 g, 0.382 mol) in anhydrous THF (382 mL) under a nitrogen atmosphere at −20° C. was added a solution of LiHMDS (1.0M in THF, 401 mL, 0.401 mol) over 50 min. The internal temperature increased to −5° C. over the course of this addition. Stirring was continued at this temperature for an additional hour. The reaction was cooled to −10° C. and a solution of 4-cyanobenzyl bromide (78.5 g, 401 mmol) in anhydrous THF (400 mL) was added over 50 min The reaction temperature had increased to 0° C. over the course of the addition. Stirring was continued for 2 h while the reaction was allowed to warm to 10° C. To the reaction mixture was added saturated aqueous $NH_4Cl$ (200 mL), water (800 mL), and EtOAc (1 L). The layers were separated and the aqueous layer was extracted with EtOAc (1 L). The combined organic layers were dried with $MgSO_4$ and concentrated in vacuo to give 214.2 g of the title compound as a tan/brown solid, m/z 571.3 $[M+MeCN+H]^+$.

(R)-2-(4-Cyano-phenyl)-1-(3,5-dichloro-4-fluoro-phenylcarbamoyl)-1-methyl-ethyl-ammonium toluene-4-sulfonate

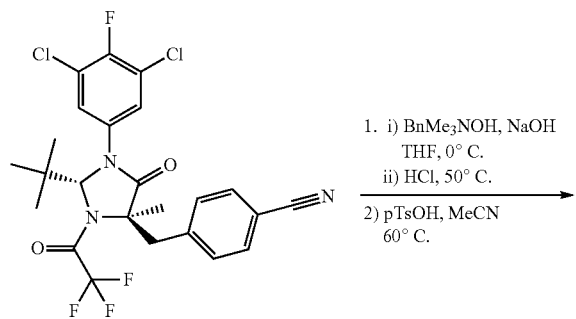

1. i) BnMe₃NOH, NaOH
   THF, 0° C.
   ii) HCl, 50° C.
2) pTsOH, MeCN
   60° C.

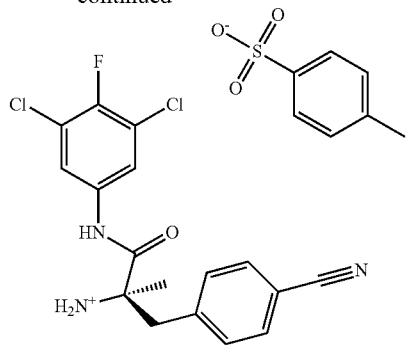

To a solution of 4-[(2R,4R)-2-tert-butyl-1-(3,5-dichloro-4-fluoro-phenyl)-4-methyl-5-oxo-3-(2,2,2-trifluoro-acetyl)-imidazolidin-4-ylmethyl]-benzonitrile (121.3 g, 228.7 mmol) in THF (457 mL) at 0° C. was added an aqueous solution of $BnMe_3NOH$ (40 wt % in water, 135.3 mL, 343.1 mmol) over 30 min followed by aqueous NaOH (50 wt %, 21.5 mL, 407 mmol). Both reagents were added at a rate sufficient to keep the internal temperature at 0° C. The reaction mixture was stirred at this temperature for 6.5 h. HCl solution (6 N, 234 mL, 1.40 mol) was then added to the reaction mixture at a rate sufficient to keep the internal temperature below 15° C. The reaction was heated to 50° C. and stirred at this temperature for 1.5 h. A portion of the solvent (~350 mL) was removed in vacuo and $CH_2Cl_2$ (300 mL) was added. The mixture was cooled in an ice bath and a NaOH solution (2 N) was added at a rate to keep the internal temperature below 20° C. until the pH of aqueous layer reached 14. The mixture was transferred to a separatory funnel using $CH_2Cl_2$ and $H_2O$ to ensure the transfer all of the solid material. The layers were separated and the aqueous layer was extracted with $CH_2Cl_2$ (2×500 mL). The combined organic layers were washed once with brine (300 mL), dried with $Na_2SO_4$, and concentrated in vacuo to give 83.8 g of a red/black viscous oil. This material was dissolved in MeCN (600 mL) and heated to 60° C. with stirring. p-Toluenesulfonic acid monohydrate (50.1 g, 263 mmol) was added to the solution causing a precipitate to form. Additional MeCN (200 mL) was added and mixture was filtered to collect the solids. The filter cake washed with 600 mL of MeCN and dried to give 106 g of the title compound as a white solid, m/z 366.6 $[M]^+$.

(R)-3-(4-Cyano-phenyl)-N-(3,5-dichloro-4-fluoro-phenyl)-2-[3-(2,2-dimethoxy-ethyl)-ureido]-2-methyl-propionamide

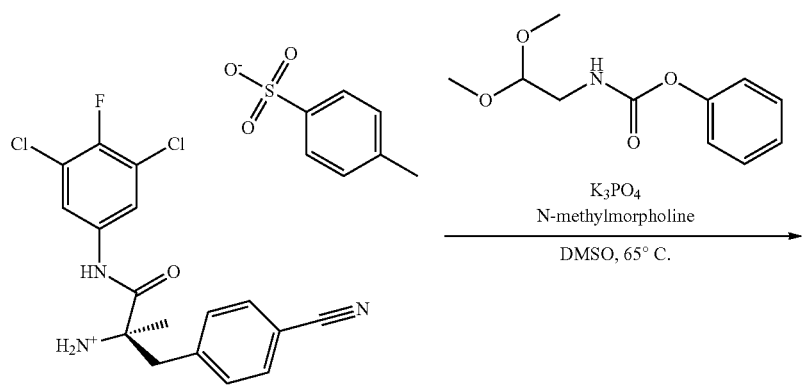

$K_3PO_4$
N-methylmorpholine

DMSO, 65° C.

-continued

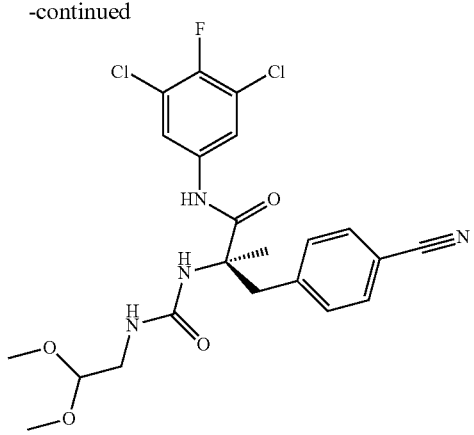

To a solution of (R)-2-(4-cyano-phenyl)-1-(3,5-dichloro-4-fluoro-phenylcarbamoyl)-1-methyl-ethyl-ammonium toluene-4-sulfonate (87.7 g, 162.9 mmol) and (2,2-dimethoxy-ethyl)-carbamic acid phenyl ester (40.4 g, 179 mmol) in DMSO (162 mL) was added $Na_3PO_4$ (29.4 g, 179 mmol) and N-methylmorpholine (3.04 mL, 27.7 mmol). The solution was heated to 65° C. and stirred for 6 h. The solution was cooled to 20° C. and transferred to a separatory funnel with aqueous $Na_2CO_3$ (3 wt %, 500 mL) and EtOAc (500 mL), forming a triphasic system after shaking. The bottom two layers were removed. The top organic layer was washed with 3% NaCl (500 mL), dried with $Na_2SO_4$ and concentrated in vacuo keeping internal temperature lower than 40° C. A mixture of heptane and EtOAc (10:1 heptane:EtOAc, 20 mL) was added and the resulting slurry was stirred at 22° C. for 16 h. The slurry was filtered and the solids were washed with a 10:1 mixture of heptane/EtOAc (2×100 mL) to give 61.6 g of the title compound as a white solid, m/z 497.7 $[M+H]^+$.

4-[(R)-1-(3,5-Dichloro-4-fluoro-phenyl)-3-methyl-2-oxo-2,3-dihydro-1,1-imidazo[1,2-a]imidazol-3-ylmethyl]-benzonitrile

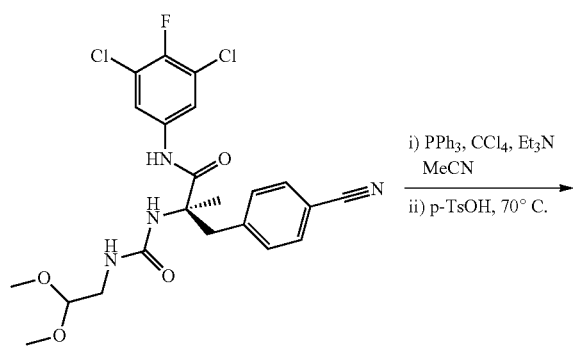

To a room temperature suspension of (R)-3-(4-cyano-phenyl)-N-(3,5-dichloro-4-fluoro-phenyl)-2-[3-(2,2-dimethoxy-ethyl)-ureido]-2-methyl-propionamide (62.6 g, 125 mmol), $PPh_3$ (51.98 g, 198 mmol), and $Et_3N$ (29.35 mL, 210.6 mmol) in MeCN (250 mL) was added $CCl_4$ (20.3 mL, 210 mmol) in one portion. The reaction was stirred for 2 h and then cooled to 0° C. To this solution was added p-toluenesulfonic acid monohydrate (37.7 g, 198 mmol) and the reaction was heated at 70° C. for 2 h. The volatiles were evaporated in vacuo, and the residue was diluted with isopropyl acetate (i-PrOAc) (500 mL) and water (500 mL). The water layer was removed and the organic layer was washed with aqueous $Na_2CO_3$ (5 wt %, 500 mL) and then aqueous NaCl (3 wt %, 500 mL). The organic layer was dried over $Na_2SO_4$ and concentrated in vacuo to give an oily solid. A mixture of Heptane/i-PrOAc (150 mL, 80:20 heptane:i-PrOAc) was added causing precipitation of a solid. The resulting slurry was stirred overnight and then filtered. The filtrate was evaporated in vacuo to give a brown oil. The oil was re-processed using the same conditions 3 more times. The remaining brown oil from the filtrate was then purified by flash chromatography on silica gel (20-50% EtOAc/hexanes) to give 48.0 g of the title compound as a white solid, m/z 415.7 $[M+H]^+$.

4-[(R)-1-(3,5-Dichloro-4-fluoro-phenyl)-5-iodo-3-methyl-2-oxo-2,3-dihydro-1H-imidazo[1,2-a]imidazol-3-ylmethyl]-benzonitrile

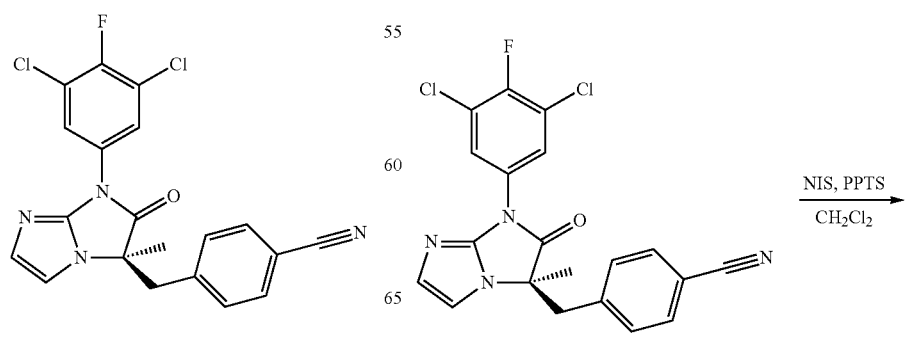

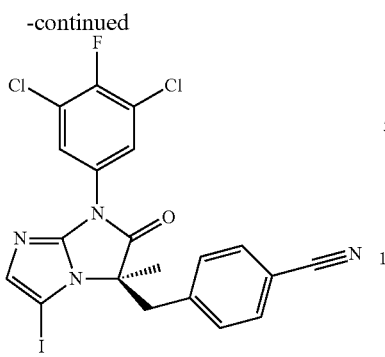

A flask containing a solution of 4-[(R)-1-(3,5-dichloro-4-fluoro-phenyl)-3-methyl-2-oxo-2,3-dihydro-1H-imidazo[1,2-a]imidazol-3-ylmethyl]-benzonitrile (48.8 g, 117 mmol) in CH$_2$Cl$_2$ (900 mL) was covered with aluminum foil and partially submerged in an ice water bath. To this solution was added a solid mixture of N-iodosuccinimide (29.1 g, 129 mmol) and pyridinium p-toluenesulfonate (2.95 g, 11.7 mmol) in four separate portions over a 30 min period. The reaction was allowed to stir in the thawing ice bath for 1 h and then the bath was removed. Stirring was continued overnight. Saturated aqueous Na$_2$S$_2$O$_3$ (300 mL) was added to the reaction and the mixture was transferred to a separatory funnel using CH$_2$Cl$_2$ (200 mL) and water (1 L). The layers were separated and the aqueous layer was further extracted with CH$_2$Cl$_2$ (2×500 mL) and EtOAc (500 mL). The combined organic layers were dried over MgSO$_4$ and concentrated in vacuo to give a yellow oil. This oil was purified by flash chromatography on silica gel (0-2.5% EtOAc/toluene) to give 52 g of the title compound as a white solid, m/z 541.3 [M+H]$^+$.

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid Acetic anhydride (14.0 mL, 148 mmol), sodium formate (15.1 g, 222 mmol) and Hunig's base (25.8 mL, 148 mmol) were suspended in anhydrous DMF (50 mL) in a 1000 mL screw-top glass pressure-vessel. The vessel was sealed with the screw cap and the mixture was allowed to stir for 45 min at room temperature. To this mixture was added a solution of 4-[(R)-1-(3,5-dichloro-4-fluoro-phenyl)-5-iodo-3-methyl-2-oxo-2,3-dihydro-1H-imidazo[1,2-a]imidazol-3-ylmethyl]-benzonitrile (40.0 g, 73.9 mmol) in anhydrous DMF (200 mL) followed by Pd(OAc)$_2$ (830 mg, 3.70 mmol) and anhydrous LiCl (9.40 g, 221 mmol). The vessel was capped tightly and allowed to stir at 80° C. for 20 h. In a well ventilated fume hood, the reaction was cooled to room temperature and the screw cap was slowly removed allowing for gas release. The reaction was transferred to a seperatory funnel containing a solution of aqueous HCl (2N, 1 L) using EtOAc (1 L). The layers were separated and the organic phase was washed with aqueous 2N HCl (1 L). The combined aqueous phase was extracted with EtOAc (2×1 L). The combined organic phase was dried with MgSO$_4$ and concentrated in vacuo. Toluene was added to the dark colored residue causing precipitation of a solid. The solid was filtered and washed with 1:1 toluene:hexanes followed by hexanes. The filtrate was concentrated and re-processed in a similar manner to give additional solids. A total of 29.4 g of the title compound was obtained as an off-white solid, m/z. 459.4 [M+H]$^+$.

The following intermediates were synthesized in a similar manner to that described above (R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid (R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid (R)-5-(4-Cyano-benzyl)-7-(3,5-dichloro-phenyl)-5-methyl-6-oxo-6,7-dihydro-5H-imidazo[1,2-a]imidazole-3-carboxylic acid 1-{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarboxylic acid

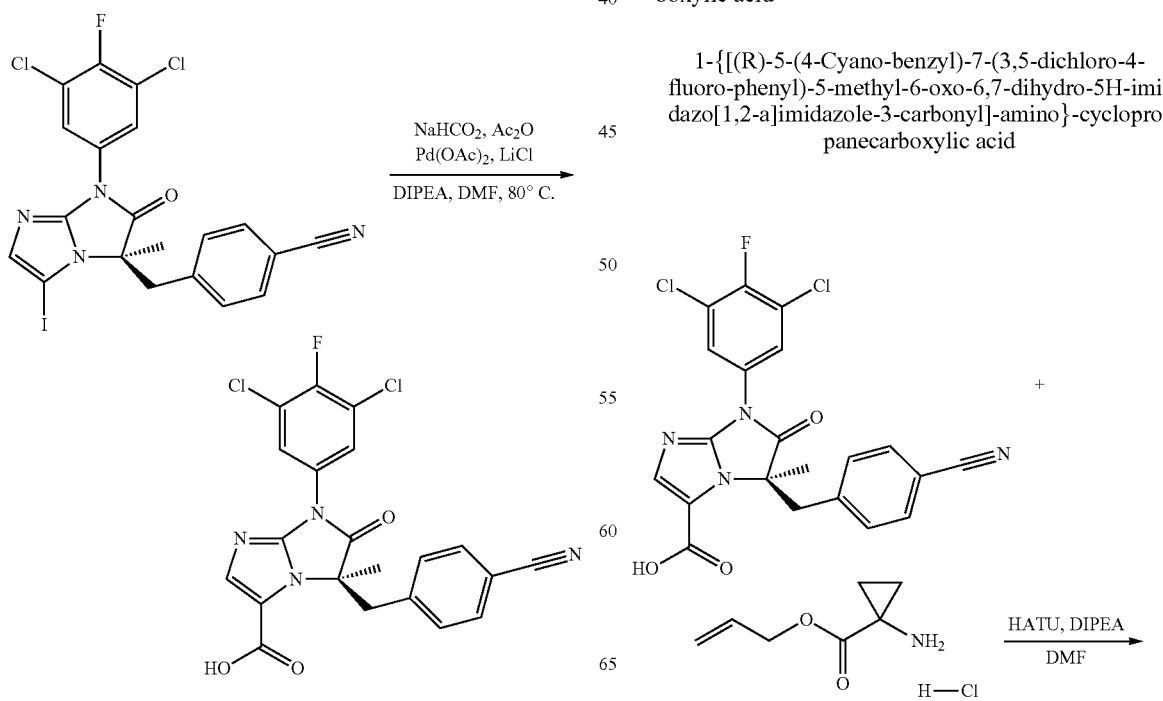

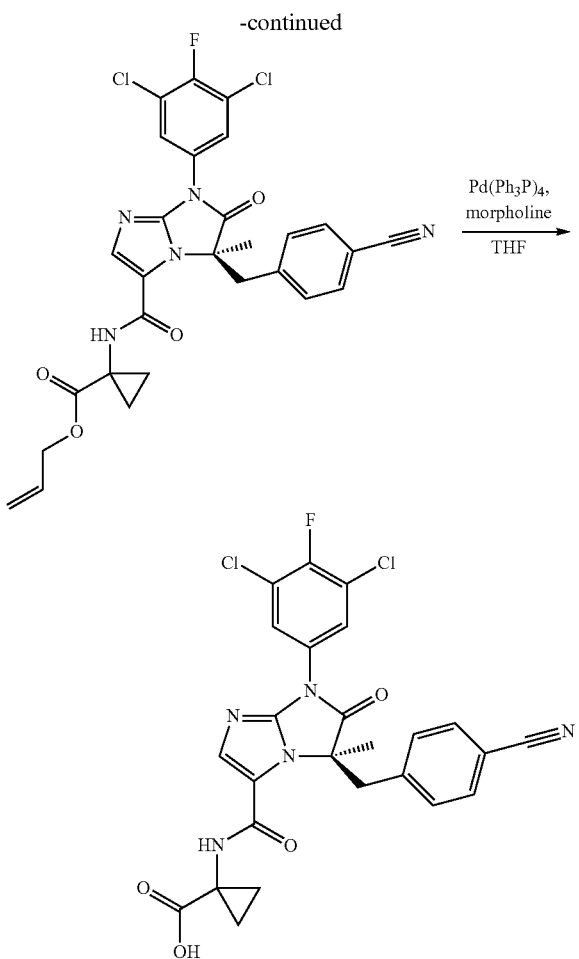

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid (10 g, 22 mmol), was added to a 500 mL round bottomed flask containing THF (100 mL). To this solution was added HATU (9.1 g, 24 mmol), diisopropylethylamine (11 mL, 65 mmol) and 1-amino-cyclopropane-carboxylic acid allyl ester hydrochloride (4.3 g, 24 mmol). The reaction was allowed to stir at room temperature for 18 h. The organics were washed with water (2×30 mL) and brine (1×30 mL) then dried (MgSO₄) and concentrated to afford crude 1-{[(R)-5-(4-cyano-benzyl)-7-(3,5-dichloro-4-fluoro-phenyl)-5-methyl-6-oxo-6,7-dihydro-5H-imidazol[1,2-a]imidazole-3-carbonyl]-amino}-cyclopropanecarboxylic acid allyl ester (12.6 g, 22 mmol) which was taken onward without further purification.

The ester obtained (12.6 g, 22 mmol) was combined with THF (100 mL). Morpholine (18.6 mL, 210 mmol) and Pd(PPh₃)₄ (500 mg, 0.40 mmol) were added and the reaction was allowed to stir at room temperature for 16 h. The solution was filtered through diatomaceous earth and then concentrated. The residue was diluted with ethyl acetate (150 mL) washed with water (2×50 mL), 1M HCl (2×50 mL), brine (1×50 mL) and then dried (MgSO₄), filtered and concentrated. The residue was purified by flash chromatography (silica-gel) using 10-100% ethyl acetate in hexanes to provide 10.4 g of the title compound.

The following intermediates were synthesized in a similar manner to that described above
1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarboxylic acid:
1-{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid:
1-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarboxylic acid:

6-Iodo-pyridine-2-carbonitrile

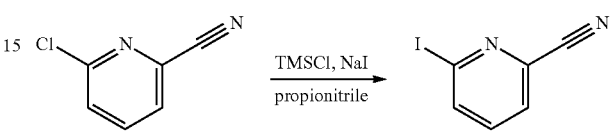

6-Chloro-pyridine-2-carbonitrile (5.0 g, 36 mmol) was taken up in propionitrile (35 mL). To this was added TMSCl (4.6 mL, 36 mmol) and sodium iodide (16.0 g, 108 mmol) and the solution was heated to 90° C. for 16 h. The solution was cooled and quenched by the addition of 2M sodium hydroxide (35 mL) The mixture was extracted with ethyl acetate (3×30 mL) and washed with water (1×50 mL) and saturated aqueous sodium bisulfate. The combined organic layers were dried over sodium sulfate and concentrated. The residue was purified by flash chromatography (silica-gel) using 0-100% ethyl acetate in hexanes to afford 4.6 g of the title compound.

1-(5-Iodo-pyridin-2-yl)-cyclopropylamine

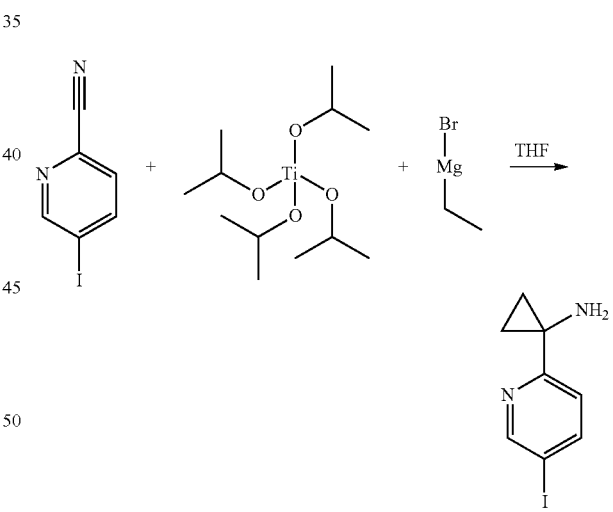

To a solution of 5-iodo-pyridine-2-carbonitrile (1.0 g, 8.1 mmol) in dry THF (50 mL) was added titanium(IV) isopropoxide (5.2 mL, 18 mmol). EtMgBr (3.0M in Et₂O, 10 mL, 32 mmol) was then added dropwise. The reaction mixture was stirred for 23 h, then diluted with water (100 mL) and 1N HCl (5 mL), and stirred for 5 minutes. The mixture was filtered and the filtrate was concentrated in-vacuo to afford 430 mg of the title compound which was used without further purification.

The following intermediates were synthesized in a similar manner to that described above
1-(4-Iodo-pyridin-2-yl)-cyclopropylamine
1-(6-Iodo-pyridin-2-yl)-cyclopropylamine (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(5-iodo-pyridin-2-yl)-cyclopropyl-carbamoyl]-cyclopropyl}-amide

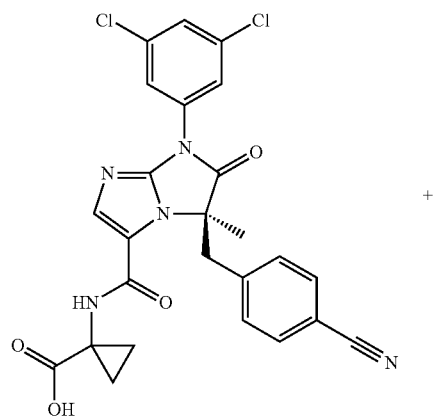

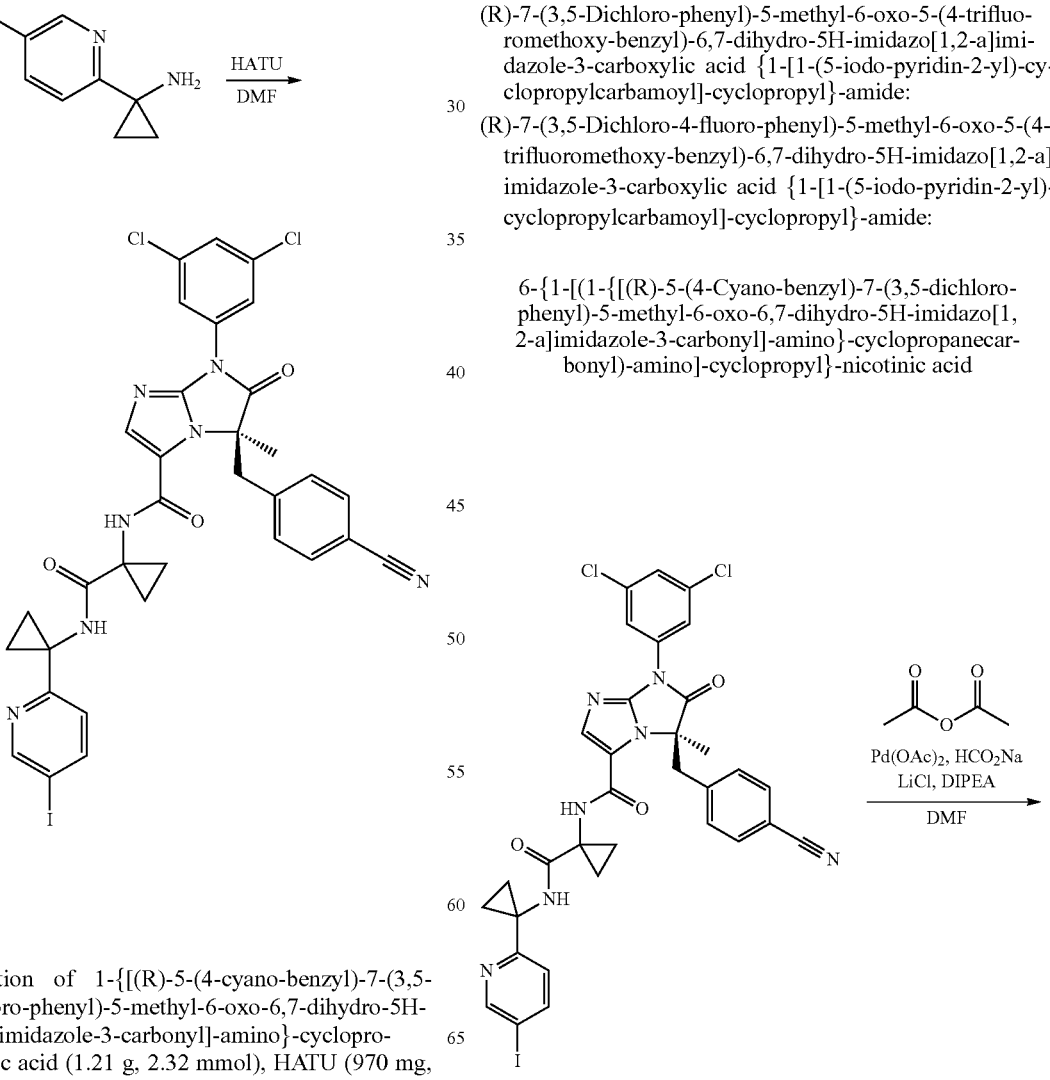

To a solution of 1-{[(R)-5-(4-cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropane-carboxylic acid (1.21 g, 2.32 mmol), HATU (970 mg, 2.55 mmol) and diisopropyl-ethylamine (808 µL, 4.64 mmol) in DMF (4 mL) was added 1-(5-iodo-pyridin-2-yl)-cyclopropylamine (724 mg, 2.78 mmol). The mixture was stirred for 1.5 h and then diluted with EtOAc (30 mL). The layers were separated and the organic layer was washed with water (3×30 mL) and brine (1×25 mL), dried with MgSO$_4$, filtered, and concentrated to afford a crude solid. The crude material was purified by flash chromatography on silica gel, eluting with 50% hexanes in ethyl acetate (and increasing polarity to 75% ethyl acetate) to afford 1.60 g of the title compound:

The following intermediates were synthesized in a similar manner to that described above (R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(4-iodo-pyridin-2-yl)-cyclopropylcarbamoyl]-cyclopropyl}-amide:

(R)-5-(4-Cyano-benzyl)-7-(3,5-dichloro-phenyl)-5-methyl-6-oxo-6,7-dihydro-5H-imidazo[1,2-a]imidazole-3-carboxylic acid {1-[1-(6-iodo-pyridin-2-yl)-cyclopropylcarbamoyl]-cyclopropyl}-amide:

(R)-5-(4-Cyano-benzyl)-7-(3,5-dichloro-4-fluoro-phenyl)-5-methyl-6-oxo-6,7-dihydro-5H-imidazo[1,2-a]imidazole-3-carboxylic acid {1-[1-(5-iodo-pyridin-2-yl)-cyclopropylcarbamoyl]-cyclopropyl}-amide:

(R)-7-(3,5-Dichloro-phenyl)-5-methyl-6-oxo-5-(4-trifluoromethoxy-benzyl)-6,7-dihydro-5H-imidazo[1,2-a]imidazole-3-carboxylic acid {1-[1-(5-iodo-pyridin-2-yl)-cyclopropylcarbamoyl]-cyclopropyl}-amide:

(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carboxylic acid {1-[1-(5-iodo-pyridin-2-yl)-cyclopropylcarbamoyl]-cyclopropyl}-amide:

6-{1-[(1-{[(R)-5-(4-Cyano-benzyl)-7-(3,5-dichlorophenyl)-5-methyl-6-oxo-6,7-dihydro-5H-imidazo[1,2-a]imidazole-3-carbonyl]-amino}-cyclopropanecarbonyl)-amino]-cyclopropyl}-nicotinic acid -continued

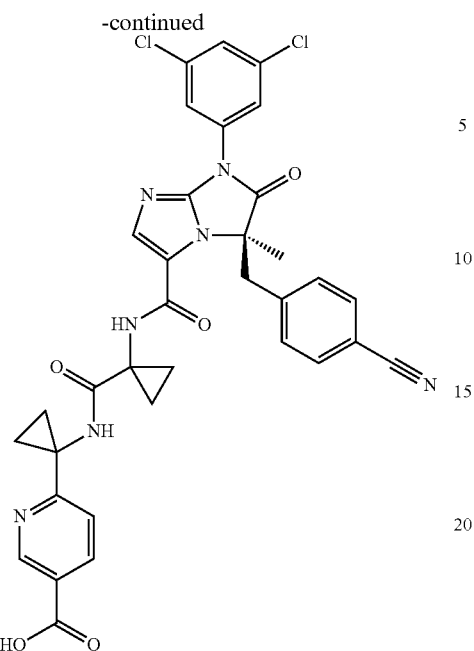

Acetic anhydride (0.58 mL, 6.13 mmol), sodium formate (625 mg, 9.19 mmol) diisopropylethylamine (1.06 mL, 6.13 mmol) and anhydrous DMF (10 mL) were added to a 50 mL glass pressure tube. The cap was sealed and reaction allowed to stir for 30 min To this mixture was then added (R)-5-(4-cyano-benzyl)-7-(3,5-dichloro-phenyl)-5-methyl-6-oxo-6,7-dihydro-5H-imidazo[1,2-a]imidazole-3-carboxylic acid {1-[1-(4-iodo-pyridin-2-yl)-cyclopropylcarbamoyl]-cyclopropyl}-amide (2.35 g, 3.07 mmol) as a solution in 5 mL of anhydrous DMF, followed by lithium chloride (389 mg, 9.19 mmol) and palladium acetate (34 mg, 0.15 mmol). The mixture was capped and then allowed to stir at 80° C. in an oil bath overnight (20 h). The reaction was cooled to room temperature. The reaction was diluted with 2N HCl (15 mL) and extracted with ethyl acetate (2×20 mL). The combined organics were dried (MgSO$_4$) and concentrated. The residual material was dissolved in DMF and purified by reversed phase HPLC using 30-100% CH$_3$CN/H$_2$O as gradient to afford 1.56 g of the title compound.

The following intermediates were synthesized in a similar manner:

2-{1-[(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-isonicotinic acid 6-{1-[(1{[(R)-5-(4-Cyano-benzyl)-7-(3,5-dichloro-4-fluoro-phenyl)-5-methyl-6-oxo-6,7-dihydro-5H-imidazo[1,2-a]imidazole-3-carbonyl]-amino}-cyclopropanecarbonyl)-amino]-cyclopropyl}-nicotinic acid 6-{1-[(1-{[(R)-5-(4-Cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridine-2-carboxylic acid 6-{1-[(1-{[(R)-7-(3,5-Dichloro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarbonyl)-amino]-cyclopropyl}-nicotinic acid 6-{1-[(1-{[(R)-7-(3,5-Dichloro-4-fluoro-phenyl)-5-methyl-6-oxo-5-(4-trifluoromethoxy-benzyl)-6,7-dihydro-5H-imidazo[1,2-a]imidazole-3-carbonyl]-amino}-cyclopropanecarbonyl)-amino]-cyclopropyl}-nicotinic acid Synthesis of Final Compounds Example 1

(3R)-3-(4-Cyanobenzyl)-1-(3,5-dichlorophenyl)-N-{1-[(1-{4-[(1-hydroxy-2-methylpropan-2-yl)carbamoyl]pyridin-2-yl}cyclopropyl)carbamoyl]-cyclopropyl}-3-methyl-2-oxo-2,3-dihydro-1H-imidazo[1,2-a]imidazole-5-carboxamide

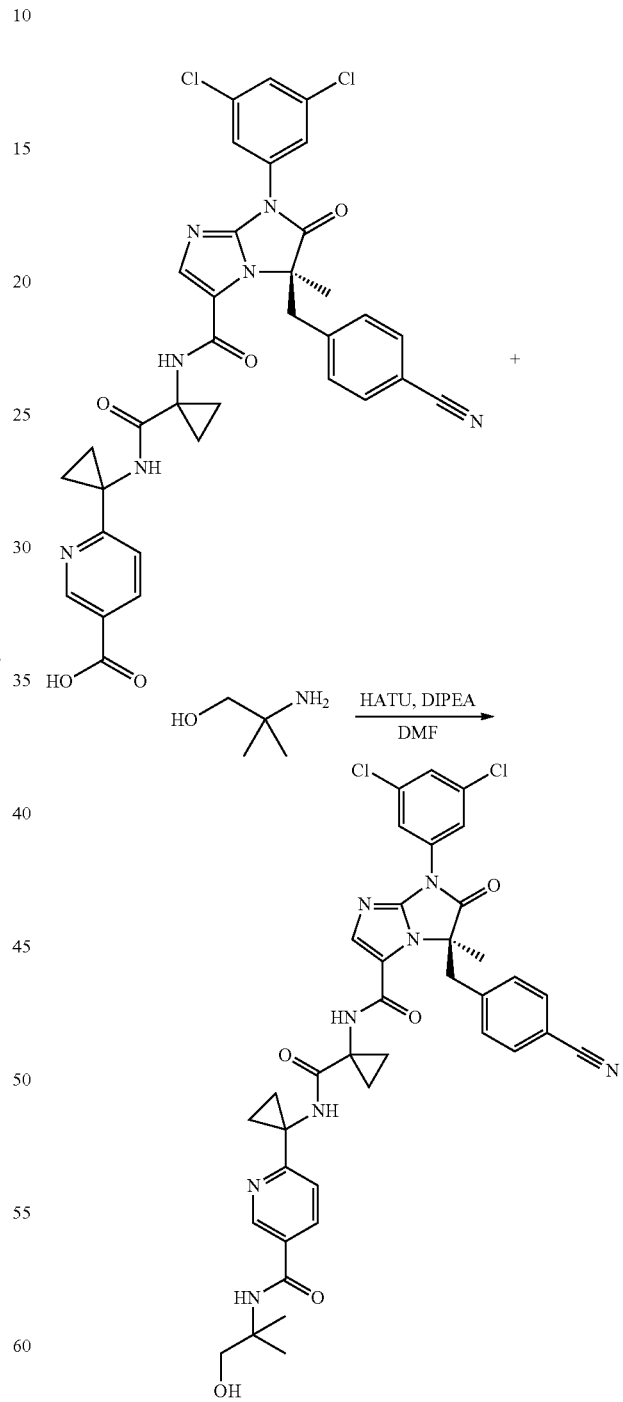

To a stirred solution of 2-{1-[(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-isonicotinic acid (30 mg, 0.044 mmol), in 3 mL DMF was added HATU (25 mg, 0.66 mmol) diisopropylethylamine (0.3 mL) and 2-amino-2-methyl-propan-1-ol (5.8 mg, 0.66 mmol). The solution was allowed to stir at room temperature overnight (18 h). The reaction was diluted with water (5 mL), then extracted with a 5% methanol/dichloromethane solution (3×10 mL). The organic layers were combined, dried (MgSO$_4$) and concentrated. The resulting oil was purified by reversed phase HPLC to afford 28 mg of the title compound, m/z 755.7.

The following compounds were synthesized in a manner similar to that described above:

| Compound | m/z |
| --- | --- |
| 1 | 780.4 |
| 2 | 830.3 |
| 3 | 763.3 |
| 4 | 727.3 |
| 5 | 753.3 |
| 6 | 788.3 |
| 7 | 781.4 |
| 8 | 780.3 |
| 9 | 751.3 |
| 10 | 787.3 |
| 11 | 737.4 |
| 12 | 788.4 |
| 13 | 737.3 |
| 14 | 740.3 |
| 15 | 794.4 |
| 16 | 751.4 |
| 17 | 742.6 |
| 18 | 781.4 |
| 20 | 741.4 |
| 21 | 774.3 |
| 22 | 794.4 |
| 23 | 794.4 |
| 24 | 773.3 |
| 25 | 773.4 |
| 26 | 774.4 |
| 27 | 741.3 |
| 28 | 780.4 |
| 29 | 781.3 |
| 30 | 727.3 |
| 31 | 697.7 |
| 32 | 787.3 |
| 33 | 787.3 |
| 34 | 741.3 |
| 35 | 727.3 |
| 36 | 774.3 |
| 37 | 766.4 |
| 38 | 711.7 |
| 41 | 741.3 |
| 42 | 753.3 |
| 43 | 794.3 |
| 44 | 781.4 |
| 45 | 808.4 |
| 46 | 788.3 |
| 47 | 788.4 |
| 48 | 753.3 |
| 49 | 742.8 |
| 50 | 774.3 |
| 51 | 739.4 |
| 52 | 684.4 |
| 53 | 787.4 |
| 54 | 794.3 |
| 55 | 723.9 |
| 57 | 754.4 |
| 58 | 753.3 |
| 59 | 737.3 |
| 60 | 741.9 |
| 61 | 780.4 |
| 62 | 754.3 |
| 63 | 754.4 |
| 64 | 774.7 |
| 65 | 787.3 |
| 66 | 757.4 |
| 67 | 780.4 |
| 68 | 768.4 |
| 69 | 755.8 |
| 70 | 794.3 |
| 71 | 737.3 |
| 72 | 774.3 |
| 73 | 741.3 |
| 74 | 741.4 |
| 75 | 741.4 |
| 76 | 763.3 |
| 77 | 797.4 |
| 78 | 726.3 |
| 79 | 774.3 |
| 80 | 781.4 |
| 81 | 773.3 |
| 82 | 800.8 |
| 83 | 754.4 |
| 84 | 788.3 |
| 85 | 781.4 |
| 86 | 755.7 |
| 87 | 739.3 |
| 88 | 760.8 |
| 89 | 830.3 |
| 90 | 723.3 |
| 91 | 741.8 |
| 92 | 774.4 |
| 93 | 788.3 |
| 94 | 743.4 |
| 95 | 788.3 |
| 96 | 757.3 |
| 98 | 683.7 |
| 99 | 741.7 |
| 100 | 741.3 |
| 101 | 794.3 |
| 102 | 754.3 |
| 103 | 753.3 |
| 104 | 723.3 |
| 105 | 755.8 |
| 106 | 754.4 |
| 107 | 754.3 |
| 108 | 801.3 |
| 109 | 777.3 |
| 110 | 751.4 |
| 111 | 780.4 |
| 112 | 754.3 |
| 113 | 794.4 |
| 114 | 737.3 |
| 115 | 780.3 |
| 116 | 808.3 |
| 117 | 755.7 |
| 118 | 787.4 |
| 119 | 737.3 |
| 120 | 741.3 |
| 121 | 768.3 |
| 122 | 780.4 |
| 123 | 723.4 |
| 124 | 712.3 |
| 125 | 781.4 |
| 126 | 723.3 |
| 127 | 740.3 |
| 128 | 741.8 |
| 129 | 757.3 |
| 130 | 753.3 |
| 131 | 741.2 |
| 132 | 768.3 |
| 133 | 757.3 |
| 134 | 787.3 |
| 135 | 737.3 |
| 136 | 741.9 |
| 137 | 781.3 |
| 138 | 739.7 |
| 139 | 788.3 |
| 140 | 697.7 |
| 141 | 741.8 |
| 142 | 737.3 |
| 143 | 753.4 |
| 144 | 788.3 |
| 145 | 753.4 |
| 146 | 741.3 |
| 147 | 794.3 |
| 148 | 683.7 |
| 149 | 788.3 |

| Compound | m/z |
|---|---|
| 150 | 741.4 |
| 151 | 788.4 |
| 152 | 801.4 |
| 153 | 830.3 |
| 154 | 741.3 |
| 155 | 788.3 |
| 156 | 766.4 |
| 157 | 766.4 |
| 158 | 794.3 |
| 159 | 777.3 |
| 160 | 788.7 |
| 161 | 781.4 |
| 162 | 774.4 |
| 163 | 780.3 |
| 164 | 702.4 |
| 165 | 787.4 |
| 166 | 754.3 |
| Compound | m/z |
|---|---|
| 167 | 801.4 |
| 168 | 753.3 |
| 169 | 788.3 |
| 170 | 794.4 |
| 171 | 794.3 |
| 172 | 740.3 |
Example 2
(R)-5-(4-Cyano-benzyl)-7-(3,5-dichloro-phenyl)-5-methyl-6-oxo-6,7-dihydro-5H-imidazo[1,2-a]imidazole-3-carboxylic acid (1-{1-[5-(2-amino-ethylcarbamoyl)-pyridin-2-yl]-cyclopropylcarbamoyl}-cyclopropyl)-amide hydrochloride
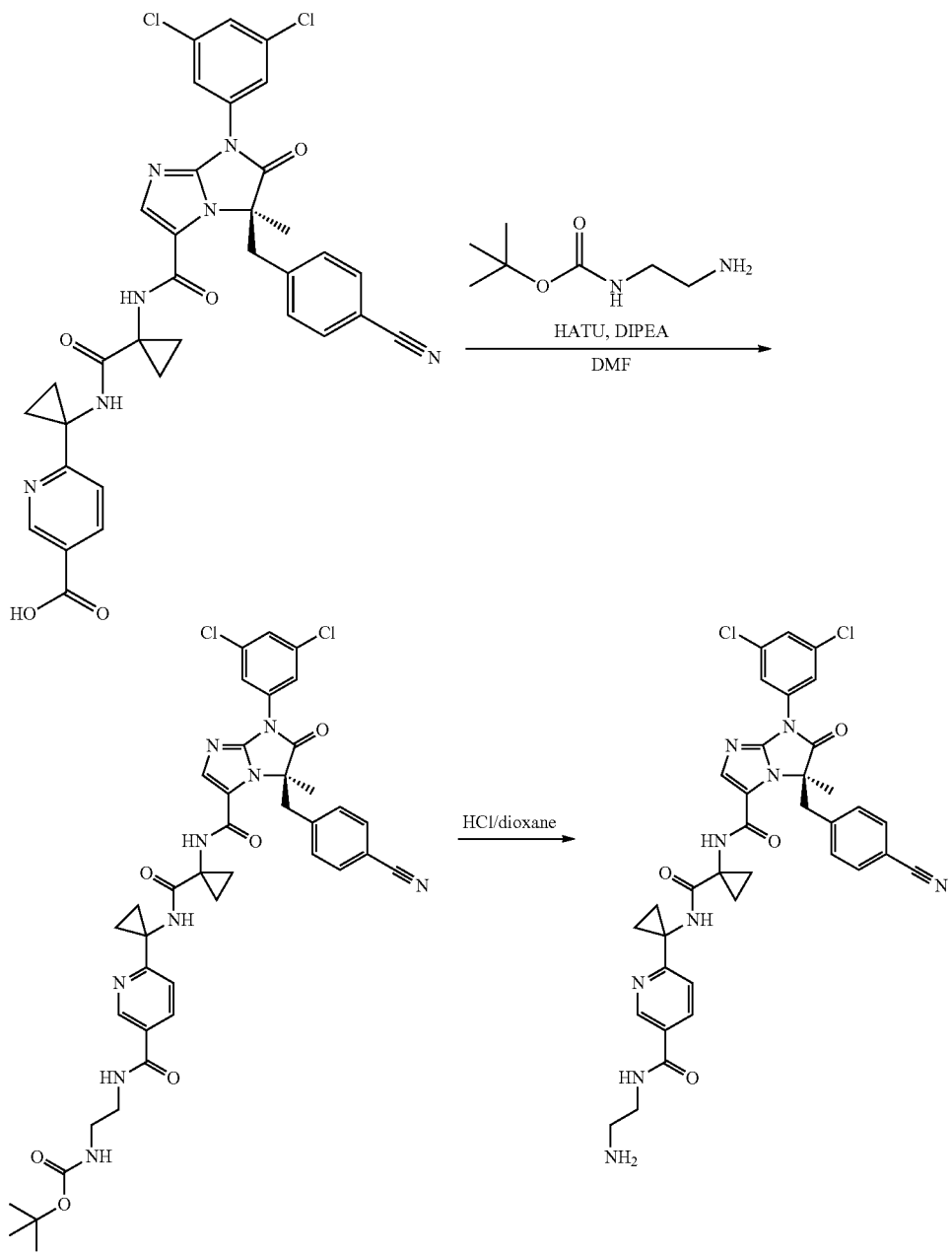

To 2-{1-[(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-isonicotinic acid (30 mg, 0.044 mmol), in DMF (3 mL) was added HATU (50 mg, 0.13 mmol) diisopropylethylamine (23 µL, 0.13 mmol) and mono-Boc-protected ethylenediamine (14 mg, 0.088 mmol). The reaction was shaken at room temperature overnight. Water was added (0.1 mL) and the crude reaction was purified by HPLC to afford {2-[(6-{1-[(1-{[(R)-5-(4-cyano-benzyl)-7-(3,5-dichloro-phenyl)-5-methyl-6-oxo-6,7-dihydro-5H-imidazo[1,2-a]imidazole-3-carbonyl]-amino}-cyclopropanecarbonyl)-amino]-cyclopropyl}-pyridine-3-carbonyl)-amino]-ethyl}-carbamic acid tert-butyl ester. This material was dissolved in dichloromethane (1.0 mL) and 4M HCl in dioxane (0.5 mL) was added. The reaction was shaken for 2 h at room temperature. The volatiles were removed to afford 23 mg of the title compound, m/z 726.3.

The following compounds were synthesized in a manner similar to that described above:

| Compound | m/z |
|---|---|
| 19 | 726.3 |
| 39 | 752.4 |
| 40 | 726.4 |
| 56 | 752.3 |
| 97 | 752.2 |

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of ICAM-1 with the Leukointegrin CD18/CD11a (LFA-1).

Description of Assay Protocol:

The LFA-1/Biotin-sICAM-1 molecular assay measures the ability of test compounds to inhibit binding of LFA-1 to Biotinylated-sICAM using AlphaScreen technology (Ref: Wilson, J, Rossi, C P, Carboni, S, Fremaux, C, Perrin, D, Soto, C, Kosco-Vilbois, M, and Scheer, A: A Homogeneous 384-Well High-Throughput Binding Assay for a TNF Receptor Using Alphascreen Technology. J Biomol Screen 2003; 8:522-532) that uses TS2/4(anti-LFA-1)-custom conjugated AlphaLisa acceptor beads and streptavidin-coated donor beads from PerkinElmer. The assay was performed in white OptiPlates-384 in a volume of 60 µL using assay buffer (Dulbecco's PBS containing calcium and magnesium, 2 mM $MgCl_2$, 0.1 mM PMSF, 0.1% BSA, pH 7.1). To each well, Biotin-sICAM was added followed by purified LFA-1 (in buffer of 50 mM triethylamine, 150 mM NaCl, 1% beta octylglucoside, 2 mM $MgCl_2$ neutralized to pH with 1M Tris-HCl, pH 7.5). For compound testing, compound was added in 5 uL to the above in 25 uL. LFA-1 and Biotin-sICAM-1 were used at concentrations that would yield a signal to background ratio of 8-10. The highest concentration of compound was 1 µM in 1% DMSO. Positive controls were wells without compound containing LFA-1, while blanks were wells without both compound and LFA-1. Plates were mixed and incubated at 37° C. for 90 minutes. This was followed by addition of 15 µL/well TS2/4-congugated acceptor beads diluted in PBS containing 0.1% BSA for a final concentration of 10 µg/mL. The plates were mixed and incubated in the dark for 30 minutes at room temperature followed by addition of 15 µL/well streptavidin-coated donor beads diluted in PBS containing 0.1% BSA at a final concentration of 15 µg/mL. The plates were mixed and incubated in the dark for 60 minutes at room temperature and then read on an EnVision Multilabel Reader using AlphaScreen 384-well OptiPlate protocol.

Compounds made in the above examples were tested in this assay and each was found to have an $IC_{50} < 1$ µM. Data from this assay are given below:

| Compound # | Alphascreen $IC_{50}$ (nM) |
|---|---|
| 1 | 1.4 |
| 2 | 2.7 |
| 3 | 0.29 |
| 4 | 0.92 |
| 5 | 0.59 |
| 6 | 0.82 |
| 7 | 1.4 |
| 8 | 1.6 |
| 9 | 1.8 |
| 10 | 6.2 |
| 11 | 3.4 |
| 12 | 8.5 |
| 13 | 0.44 |
| 14 | 0.27 |
| 15 | 1.5 |
| 16 | 12 |
| 17 | 0.18 |
| 18 | 1.8 |
| 20 | 1.0 |
| 21 | 0.81 |
| 22 | 2.1 |
| 23 | 2.6 |
| 24 | 4.1 |
| 25 | 32 |
| 26 | 5.2 |
| 27 | 0.74 |
| 28 | 2.5 |
| 29 | 0.43 |
| 30 | 0.91 |
| 31 | 0.67 |
| 32 | 4.0 |
| 33 | 2.7 |
| 34 | 0.70 |
| 35 | 0.39 |
| 36 | 0.25 |
| 37 | 2.4 |
| 38 | 0.87 |
| 41 | 0.14 |
| 42 | 0.35 |
| 43 | 0.74 |
| 44 | 0.88 |
| 45 | 4.5 |
| 46 | 0.78 |
| 47 | 3.9 |
| 48 | 2.4 |
| 49 | 0.56 |
| 50 | 0.97 |
| 51 | 0.58 |
| 52 | 0.54 |
| 53 | 2.4 |
| 54 | 1.2 |
| 55 | 0.67 |
| 57 | 0.82 |
| 58 | 0.70 |
| 59 | 0.36 |
| 60 | 0.27 |
| 61 | 1.8 |

| Compound # | Alphascreen IC$_{50}$ (nM) |
|---|---|
| 62 | 1.1 |
| 63 | 1.7 |
| 64 | 0.34 |
| 65 | 2.1 |
| 66 | 0.28 |
| 67 | 2.6 |
| 68 | 0.5 |
| 69 | 0.47 |
| 70 | 0.55 |
| 71 | 0.74 |
| 72 | 0.45 |
| 73 | 0.37 |
| 74 | 1.4 |
| 75 | 2.2 |
| 76 | 0.79 |
| 77 | 1.3 |
| 78 | 0.68 |
| 79 | 0.67 |
| 80 | 0.99 |
| 81 | 1.5 |
| 82 | 0.80 |
| 83 | 1.3 |
| 84 | 0.53 |
| 85 | 0.34 |
| 86 | 0.56 |
| 87 | 0.98 |
| 88 | 1.9 |
| 89 | 1.4 |
| 90 | 0.29 |
| 91 | 0.81 |
| 92 | 1.3 |
| 93 | 0.62 |
| 94 | 1.5 |
| 95 | 1.0 |
| 96 | 0.74 |
| 98 | 1.1 |
| 99 | 0.52 |
| 100 | 0.90 |
| 101 | 0.42 |
| 102 | 0.37 |
| 103 | 0.75 |
| 104 | 2.3 |
| 105 | 0.65 |
| 106 | 0.82 |
| 107 | 0.30 |
| 108 | 3.0 |
| 109 | 0.41 |
| 110 | 3.4 |
| 111 | 2.5 |
| 112 | 0.28 |
| 113 | 1.3 |
| 114 | 0.84 |
| 115 | 0.33 |
| 116 | 0.75 |
| 117 | 0.37 |
| 118 | 33 |
| 119 | 0.72 |
| 120 | 0.75 |
| 121 | 0.37 |
| 122 | 1.7 |
| 123 | 0.34 |
| 124 | 2.1 |
| 125 | 0.28 |
| 126 | 2.6 |
| 127 | 0.5 |
| 128 | 0.47 |
| 129 | 0.55 |
| 130 | 0.74 |
| 131 | 0.45 |
| 132 | 0.37 |
| 133 | 1.4 |
| 134 | 2.2 |
| 135 | 0.79 |
| 136 | 1.3 |
| 137 | 0.68 |
| 138 | 0.67 |
| 139 | 0.99 |
| 140 | 1.5 |
| 141 | 0.80 |
| 142 | 1.3 |
| 143 | 0.53 |
| 144 | 0.34 |
| 145 | 0.56 |
| 146 | 0.98 |
| 147 | 1.9 |
| 148 | 1.4 |
| 149 | 0.29 |
| 150 | 0.81 |
| 151 | 1.3 |
| 152 | 0.62 |
| 153 | 1.5 |
| 154 | 1.0 |
| 155 | 0.74 |
| 156 | 1.1 |
| 157 | 0.52 |
| 158 | 0.90 |
| 159 | 0.42 |
| 160 | 0.37 |
| 161 | 0.75 |
| 162 | 2.3 |
| 163 | 0.65 |
| 164 | 0.82 |
| 165 | 0.30 |
| 166 | 3.0 |
| 167 | 0.41 |
| 168 | 3.4 |
| 169 | 2.5 |
| 170 | 0.28 |
| 171 | 1.3 |
| 172 | 0.84 |
| 19 | 0.39 |
| 39 | 3.6 |
| 40 | 1.3 |
| 56 | 0.6 |
| 97 | 1.0 |

Assay to Determine Inhibition IL-2 Production in Whole Blood

Purpose of Assay:

This assay protocol is designed to study the functional antagonism, by a test compound, of the interaction of ICAM-1 with the Leukointegrin CD18/CD11a (LFA-1).

Description of Assay Protocol:

Compounds were evaluated for their ability to inhibit the production of IL-2 by cells present in freshly drawn heparinized human whole blood after stimulation ex vivo by staphylococcal enterotoxin B (SEB). Compounds were diluted in human AB serum to 11× their final assay concentration. Following further dilution for concentration response curves in human AB serum containing 1.12% DMSO, human whole blood was added to the compounds. Following a 30 minute incubation of blood and compound, SEB was then added to yield a final concentration of 600 ng/mL SEB and a final DMSO concentration of 0.1%. After overnight incubation (37° C. humidified $CO_2$ incubator), plasma samples were collected and analyzed for the presence of IL-2 using an electrochemiluminescence protocol. For this assay a biotinylated anti-human IL-2 antibody (R&D Systems BAF202), an MSD Sulfo-TAG (MSD R91AN-2) labeled anti-human IL-2 monoclonal antibody (R&D Systems MAB602), and MSD Standard Avidin plates were employed to measure IL-2 in plasma samples.

Representative compounds made in the above examples were tested in this assay and most were found to have an $IC_{50} < 10 \, \mu M$.

Assay to Determine Metabolic Stability by Human Liver Microsomes

Purpose of Assay:

This assay protocol is designed to study the stability of a test compound toward metabolic oxidation by human liver microsomes.

Description of Assay Protocol:

Compounds were incubated in human liver microsomes to estimate the disappearance $t_{1/2}$, of the parent compound. Assay was performed in 50 mM potassium phosphate buffer, pH 7.4 and 2.5 mM NADPH. Compounds were tested at a final assay concentration of 1 μM. The protein concentration was 1 mg/mL. The reaction was pre-incubated at 37° C. for 5 mM, and the metabolic reactions were initiated by the addition of NADPH. Aliquots were removed at 0, 5, and 30 minutes and were precipitated with acetonitrile containing internal standard. The samples were filtered through 0.25 mm glass fiber filter plates and the supernatant was analyzed by LC/MS/MS. Percent loss of parent compound was calculated from the peak area ratio (compound/internal standard) at each time point in comparison to the peak area ratio of the zero minute sample to determine the $t_{1/2}$, in minutes. The half life in minutes using 1 mg of microsomal protein was converted into intrinsic clearance (CLint) by scaling up the data for mg of microsomal protein/g liver and for g liver/kg body weight using the following:

$$CLint(\text{in mL/min/kg}) = 0.693/T_{1/2} * \text{mL}/1 \text{ mg} * 45 \text{ mg LM/g liver} * 25.7 \text{ g liver/kg } b.w.$$

Clint was then scaled up to estimate a whole body clearance using the well-stirred model using the following:

$CL_H(\text{in mL/min/kg}) = Q_H * CLint/(Q_H + CLint)$ where $Q_H$ is hepatic blood flow, 20.7 mL/min/kg in a human. $CL_H$ can then be expressed as a percent of $Q_H$ (% $Q_H$).

Representative compounds made in the above examples were tested in this assay and most compounds were found to be metabolized at a low to moderate rate of <75% $Q_H$.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the specific immune system in a mammal (e.g., asthma, psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus) and conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis and granulocyte transfusion associated syndrome). Preferably, the compounds of the invention can be used to treat psoriasis and multiple sclerosis.

Thus, another aspect of the invention is directed to a compound of formula I for use as a medicament and, in a particular aspect, for use as a medicament for the treatment of inflammation or an inflammatory condition. In another particular aspect, the invention is directed to a compound of formula I for use as a medicament for the treatment of any of the diseases or conditions listed in the previous paragraph. In another aspect, the invention is directed to the use of a compound of formula I for the manufacture of a medicament for the treatment of any of the diseases or conditions listed in the previous paragraph.

Thus, another aspect of the invention is the provision of a method for the treatment or prophylaxis of the above-described conditions through the administration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of a relapse in multiple sclerosis). The prophylactic administration of a compound of the formula I serves to prevent or attenuate any subsequent inflammatory response (such as, for example, a relapse in multiple sclerosis). The therapeutic administration of a compound of the formula I serves to attenuate any actual inflammation (such as, for example, a relapse in multiple sclerosis). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day, preferably in the range of 1 mg to 100 mg per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

We claim:
1. A compound of formula I:

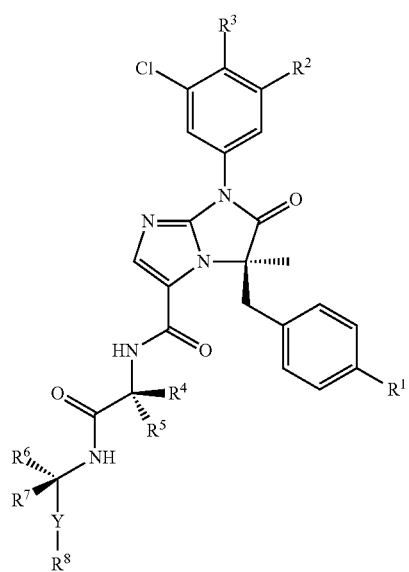

I wherein:
$R^1$ is selected from —CN and —OCF$_3$;
$R^2$ is Cl;
$R^3$ is H or F;
$R^4$ and $R^5$ together with the carbon atom they are bonded to constitute a saturated hydrocarbon ring of 3 carbon atoms;
$R^6$ and $R^7$ together with the carbon atom they are bonded to constitute a saturated hydrocarbon ring of 3 carbon atoms;
Y is a pyridyl group;
$R^8$ is —C(O)NR$^9$R$^{10}$ and is connected to the 4-, 5-, or 6-position of Y;
$R^9$ is selected from
(A) H;
(B) C$_{1-4}$alkyl, optionally substituted with one or two groups selected from:
a) —OH,
b) —C(O)NH$_2$,
c) —NHC(O)CH$_3$,
d) —COOH,
e) —OCH$_3$,
f) pyridyl,
g) furanyl,
h) imidazolyl,
i) phenyl,
j) cyclopropyl, and
k) —NR$^{11}$R$^{12}$, and
(C) C$_{3-5}$cycloalkyl;
$R^{10}$ is H, —CH$_3$, or —CH$_2$CH$_3$, or
$R^9$ and $R^{10}$ constitute a saturated hydrocarbon bridge of 3 to 5 carbon atoms which together with the N they are bonded to, form a heterocyclic ring, and wherein:
a) one carbon atom in said heterocyclic ring may be optionally substituted with —OH, —CH$_2$OH, —C(O)NH$_2$, —N(CH$_3$)$_2$, —NHC(O)CH$_3$ or —NCH$_3$C(O)CH$_3$, or
b) wherein one carbon atom in said heterocyclic ring may be optionally replaced by —O—, or —NH—, —NCH$_3$—, —NSO$_2$CH$_3$— or —NC(O)CH$_3$—;
$R^{11}$ is H or —CH$_3$;
$R^{12}$ is H or —CH$_3$;
or a pharmaceutically acceptable salt thereof.

2. A compound according to claim 1, wherein:
$R^1$ is selected from —CN and —OCF$_3$;
$R^2$ is Cl;
$R^3$ is H or F;
$R^4$ and $R^5$ together with the carbon atom they are bonded to constitute a saturated hydrocarbon ring of 3 carbon atoms;
$R^6$ and $R^7$ together with the carbon atom they are bonded to constitute a saturated hydrocarbon ring of 3 carbon atoms;
Y is

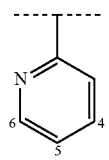

$R^8$ is —C(O)NR$^9$R$^{10}$ and is connected to the 4- or 5-position of Y;

$R^9$ is selected from
(A) H,
(B) $C_{1-4}$alkyl, optionally substituted with one or two of the following:
  a) —OH,
  b) —C(O)NH$_2$,
  c) —NHC(O)CH$_3$,
  d) —COOH,
  e) —OCH$_3$,
  f) pyridyl,
  g) furan-2-yl,
  h) 1-H-imidazol-1-yl,
  i) phenyl,
  j) cyclopropyl,
  k) —N(CH$_3$)$_2$, and
  l) —NH$_2$, and
(C) $C_{3-4}$cycloalkyl;
$R^{10}$ is —H, or —CH$_3$, or
$R^9$ and $R^{10}$ constitute a saturated hydrocarbon bridge of 3 to 5 carbon atoms which together with the N they are bonded to, form a heterocyclic ring, and wherein one carbon atom in said heterocyclic ring may be optionally substituted with —OH, —CH$_2$OH or —C(O)NH$_2$ or may be optionally replaced by —O—;
or a pharmaceutically acceptable salt thereof.

3. A compound according to claim 1, wherein:
$R^1$ is selected from —CN and —OCF$_3$;
$R^2$ is Cl;
$R^3$ is H or F;
$R^4$ and $R^5$ together with the carbon atom they are bonded to constitute a saturated hydrocarbon ring of 3 carbon atoms;
$R^6$ and $R^7$ together with the carbon atom they are bonded to constitute a saturated hydrocarbon ring of 3 carbon atoms;
Y is

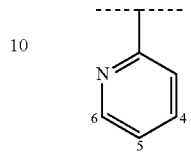

$R^8$ is —C(O)NR$^9$R$^{10}$ and is connected to the 4- or 5-position of Y;
$R^9$ is selected from
(A) H,
(B) $C_{1-4}$alkyl, optionally substituted with one of the following:
  a) —OH,
  b) —C(O)NH$_2$, or
  c) —COOH, and
(C) cyclopropyl;
$R^{10}$ is H;
or a pharmaceutically acceptable salt thereof.

4. A compound selected from the compounds in the following Table 1:

TABLE 1

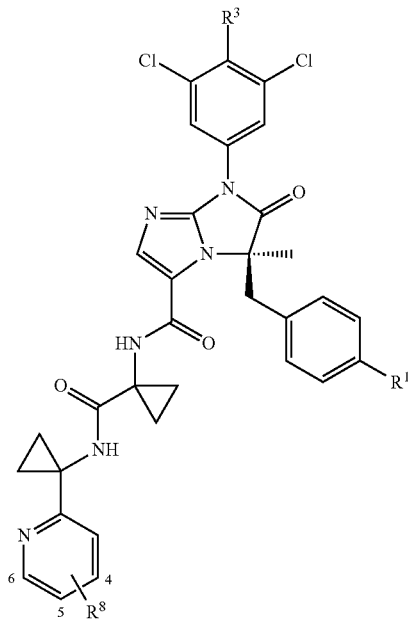

| | | | | $R^8$ | | |
|---|---|---|---|---|---|---|
| Ex | $R^1$ | $R^3$ | 6 | 5 | 4 |
| 1 | CN | H | H | H | 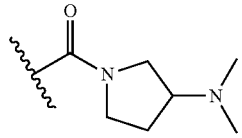 |

TABLE 1-continued

| Ex | R¹ | R³ | R⁸ 6 | R⁸ 5 | R⁸ 4 |
|---|---|---|---|---|---|
| 2 | CN | H | [piperazine-N-SO2Me acyl] | H | H |
| 3 | CN | H | H | [C(O)NHCH2-furan-2-yl] | H |
| 4 | CN | H | H | H | [C(O)NHCH2CH2OH] |
| 5 | CN | H | H | [C(O)-(3-hydroxypyrrolidin-1-yl)] | H |
| 6 | CN | H | H | H | [C(O)NHCH2CH2-pyridin-2-yl] |
| 7 | CN | H | H | H | [C(O)-(4-(hydroxymethyl)piperidin-1-yl)] |

TABLE 1-continued

| Ex | R¹ | R³ | R⁸ 6 | R⁸ 5 | R⁸ 4 |
|---|---|---|---|---|---|
| 8 | CN | H | H | [1-carbamoylpyrrolidin-2-yl carbonyl, (S)] | H |
| 9 | CN | H | H | [piperidin-1-yl carbonyl] | H |
| 10 | CN | H | H | H | [C(O)NH-CH(CH₃)-phenyl] |
| 11 | CN | H | [pyrrolidin-1-yl carbonyl] | H | H |
| 12 | CN | H | [C(O)NH-CH(CH₃)-(pyridin-2-yl)] | H | H |
| 13 | CN | H | H | [C(O)NH-CH₂-cyclopropyl] | H |

TABLE 1-continued

[Structure shown: core scaffold with R¹, R³, R⁸ substituents on pyridine positions 4, 5, 6]

| Ex | R¹ | R³ | R⁸ 6 | R⁸ 5 | R⁸ 4 |
|----|----|----|------|------|------|
| 14 | CN | H | H | ⸺C(O)NH-CH₂-C(O)NH₂ | H |
| 15 | CN | H | ⸺C(O)-N(pyrrolidin-3-yl-NHAc) | H | H |
| 16 | CN | H | ⸺C(O)-N(piperidinyl) | H | H |
| 17 | CN | H | H | H | ⸺C(O)NH-CH(CH₃)-CH₂OH |
| 18 | CN | H | ⸺C(O)-N(4-(hydroxymethyl)piperidinyl) | H | H |
| 19 | CN | H | H | H | ⸺C(O)NH-CH₂CH₂-NH₂ |

TABLE 1-continued

| Ex | R¹ | R³ | R⁸ 6 | R⁸ 5 | R⁸ 4 |
|---|---|---|---|---|---|
| 20 | CN | H | ~C(O)N(CH₃)CH₂CH₂OH | H | H |
| 21 | CN | H | H | ~C(O)NHCH₂-(3-pyridyl) | H |
| 22 | CN | H | ~C(O)-N(piperazinyl)-C(O)CH₃ | H | H |
| 23 | CN | H | ~C(O)-N(piperidin-3-yl-carboxamide) | H | H |
| 24 | CN | H | H | H | ~C(O)NHCH₂-phenyl |
| 25 | CN | H | ~C(O)NHCH₂-(2-pyridyl) | H | H |

TABLE 1-continued

| Ex | R¹ | R³ | R⁸ 6 | R⁸ 5 | R⁸ 4 |
|---|---|---|---|---|---|
| 26 | CN | H | ⸺C(O)NHCH₂-(4-pyridyl) | H | H |
| 27 | CN | H | H | ⸺C(O)NH-CH(CH₃)CH₂OH | H |
| 28 | CN | H | ⸺C(O)-N(pyrrolidine-2-C(O)NH₂) | H | H |
| 29 | CN | H | H | ⸺C(O)-N(3-hydroxymethylpiperidine) | H |
| 30 | CN | H | ⸺C(O)NHCH₂CH₂OH | H | H |
| 31 | CN | H | H | H | CONHMe |
| 32 | CN | H | H | H | ⸺C(O)NHCH₂CH₂Ph |

TABLE 1-continued

| Ex | R¹ | R³ | R⁸ 6 | R⁸ 5 | R⁸ 4 |
|---|---|---|---|---|---|
| 33 | CN | H | H | (acetamide with (S)-1-phenylethyl group) | H |
| 34 | CN | H | H | H | (N-methyl-N-(2-hydroxyethyl)carboxamide) |
| 35 | CN | H | H | (N-(2-hydroxyethyl)carboxamide) | H |
| 36 | CN | H | H | (N-(pyridin-2-ylmethyl)carboxamide) | H |
| 37 | CN | H | H | (4-methylpiperazin-1-yl carbonyl) | H |
| 38 | CN | H | H | H | CONMe₂ |
| 39 | CN | H | (piperazin-1-yl carbonyl) | H | H |

TABLE 1-continued
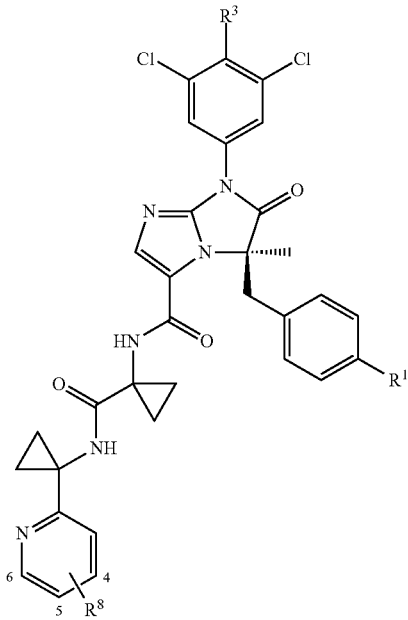
| Ex | R¹ | R³ | R⁸ 6 | R⁸ 5 | R⁸ 4 |
|---|---|---|---|---|---|
| 40 | CN | H | 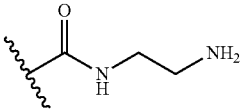 [SMILES: *C(=O)NCCN] | H | H |
| 41 | CN | H | H | 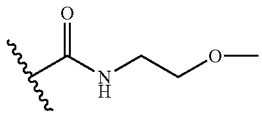 [SMILES: *C(=O)NCCOC] | H |
| 42 | CN | H | H | 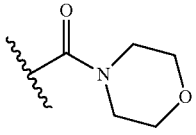 [SMILES: *C(=O)N1CCOCC1] | H |
| 43 | CN | H | H | H | 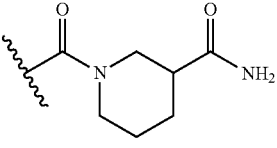 [SMILES: *C(=O)N1CCCC(C(N)=O)C1] |
| 44 | CN | H | H | H | 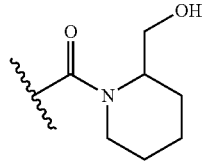 [SMILES: *C(=O)N1CCCCC1CO] |

TABLE 1-continued
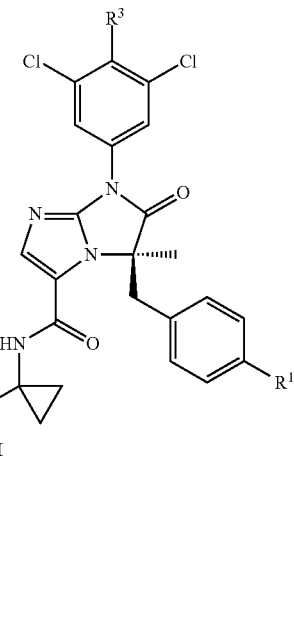
| Ex | R¹ | R³ | R⁸ 6 | R⁸ 5 | R⁸ 4 |
|---|---|---|---|---|---|
| 45 | CN | H | (1-acetyl-N-methyl-pyrrolidin-3-yl carbonyl) | H | H |
| 46 | CN | H | H | C(O)NH-CH(CH₃)-(pyridin-4-yl) | H |
| 47 | CN | H | C(O)NH-CH(CH₃)-(pyridin-3-yl) | H | H |
| 48 | CN | H | (3S)-3-hydroxypyrrolidin-1-yl carbonyl | H | H |
| 49 | CN | H | H | H | C(O)NH-CH(CH₃)-CH₂OH |
| 50 | CN | H | C(O)NH-CH₂-(pyridin-4-yl) | H | H |

TABLE 1-continued

| Ex | R¹ | R³ | R⁸ 6 | R⁸ 5 | R⁸ 4 |
|----|----|----|------|------|------|
| 51 | CN | H | ![3-hydroxyazetidine-1-carbonyl] | H | H |
| 52 | CN | H | H | H | CONH₂ |
| 53 | CN | H | H | H | ![(S)-N-(1-phenylethyl)carboxamide] |
| 54 | CN | H | H | H | ![3-acetamidopyrrolidine-1-carbonyl] |
| 55 | CN | H | H | H | ![N-cyclopropylcarboxamide] |
| 56 | CN | H | H | ![piperazine-1-carbonyl] | H |

TABLE 1-continued
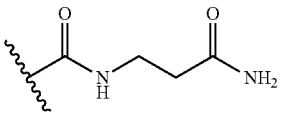 [SMILES: *C(=O)NCCC(N)=O]
| Ex | R¹ | R³ | 6 | 5 | 4 |
|---|---|---|---|---|---|
| 57 | CN | H | 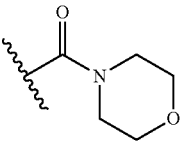 | H | H |
| 58 | CN | H | H | H | 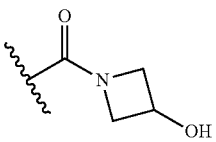 |
| 59 | CN | H | H | 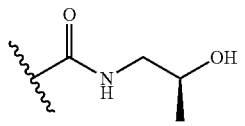 | H |
| 60 | CN | H | H | H | 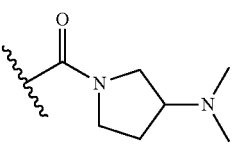 [SMILES: *C(=O)N1CCC(N(C)C)C1] |
| 61 | CN | H | H | 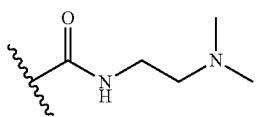 [SMILES: *C(=O)NCCN(C)C] | H |
| 62 | CN | H | H | H |  |

TABLE 1-continued
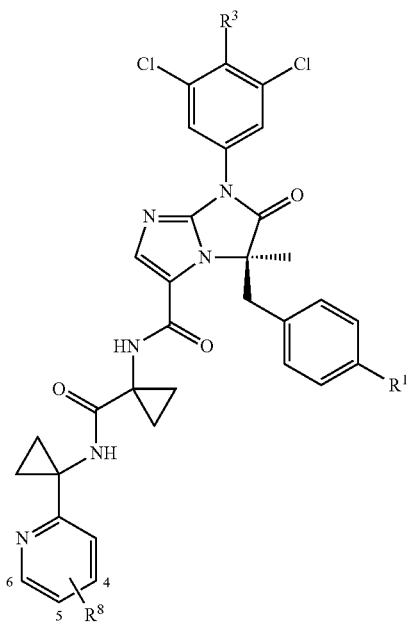
| Ex | R¹ | R³ | R⁸ 6 | R⁸ 5 | R⁸ 4 |
|----|----|----|------|------|------|
| 63 | CN | H | 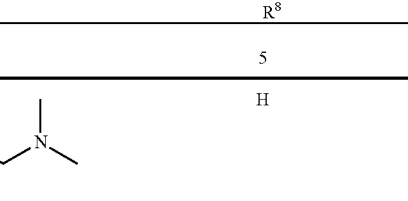 | H | H |
| 64 | CN | H | H | H | 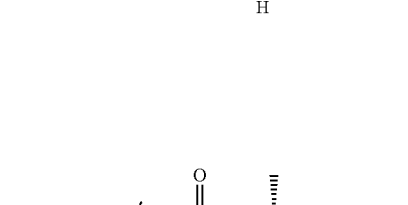 |
| 65 | CN | H | H | 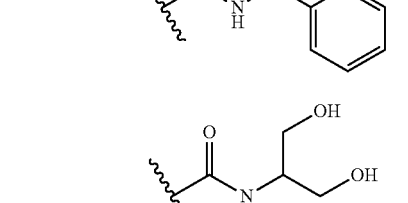 | H |
| 66 | CN | H | H | 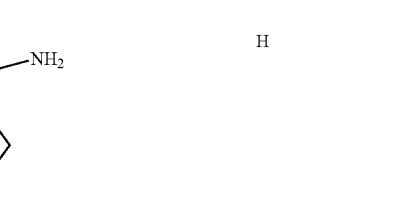 | H |
| 67 | CN | H |  | H | H |
| 68 | CN | H |  | H | H |

TABLE 1-continued

| Ex | R¹ | R³ | R⁸ 6 | R⁸ 5 | R⁸ 4 |
|---|---|---|---|---|---|
| 69 | CN | H | H | H | acetamido-2-hydroxy-2-methylpropyl |
| 70 | CN | H | H | H | 1-acyl-piperidine-4-carboxylic acid |
| 71 | CN | H | H | N-cyclobutyl amide | H |
| 72 | CN | H | H | H | N-(pyridin-3-ylmethyl)amide |
| 73 | CN | H | H | N-(2-hydroxypropyl)amide | H |
| 74 | CN | H | N-(2-hydroxypropyl)amide | H | H |

TABLE 1-continued

| Ex | R¹ | R³ | R⁸ 6 | R⁸ 5 | R⁸ 4 |
|---|---|---|---|---|---|
| 75 | CN | H | ⸝⸝⸝C(O)NH-CH₂CH₂-O-CH₃ | H | H |
| 76 | CN | H | H | H | ⸝⸝⸝C(O)NH-CH₂-(2-furyl) |
| 77 | CN | H | H | ⸝⸝⸝C(O)NH-CH₂-C(O)OH | H |
| 78 | CN | H | H | ⸝⸝⸝C(O)NH-CH₂CH₂-NH₂ | H |
| 79 | CN | H | H | H | ⸝⸝⸝C(O)NH-CH₂-(2-pyridyl) |
| 80 | CN | H | H | H | ⸝⸝⸝C(O)-N(piperidin-1-yl)-3-CH₂OH |

TABLE 1-continued
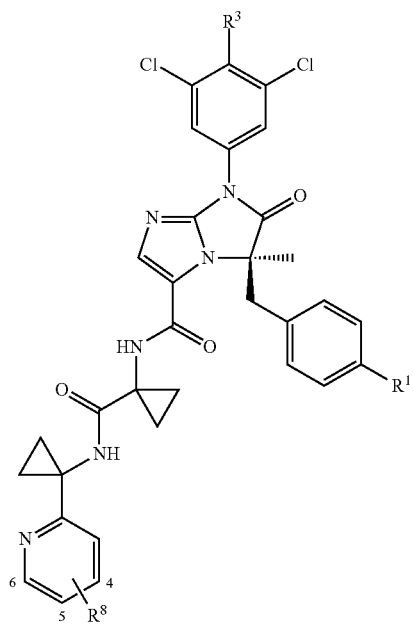
| Ex | R¹ | R³ | R⁸ 6 | R⁸ 5 | R⁸ 4 |
|---|---|---|---|---|---|
| 81 | CN | H | H | ⌇C(O)NH-benzyl | H |
| 82 | OCF₃ | F | H | ⌇C(O)NH-cyclopropyl | H |
| 83 | CN | H | ⌇C(O)NH-CH(CH₃)-C(O)NH₂ | H | H |
| 84 | CN | H | H | ⌇C(O)NH-CH₂CH₂-(3-pyridyl) | H |
| 85 | CN | H | H | ⌇C(O)-N(piperidinyl-4-CH₂OH) | H |
| 86 | CN | H | H | ⌇C(O)NH-C(CH₃)₂-CH₂OH | H |

TABLE 1-continued

| Ex | R¹ | R³ | R⁸ 6 | R⁸ 5 | R⁸ 4 |
|---|---|---|---|---|---|
| 87 | CN | H | H | H | (1-acyl-azetidin-3-ol) |
| 88 | OCF₃ | F | H | CONH₂ | H |
| 89 | CN | H | H | H | (1-acyl-4-methylsulfonyl-piperazine) |
| 90 | CN | H | H | (1-acyl-azetidine) | H |
| 91 | CN | H | H | (C(O)NH-CH(CH₃)-CH₂OH, (S)) | H |
| 92 | CN | H | (C(O)NH-CH₂-(2-pyridyl)) | H | H |
| 93 | CN | H | H | (C(O)NH-CH₂CH₂-(2-pyridyl)) | H |

TABLE 1-continued
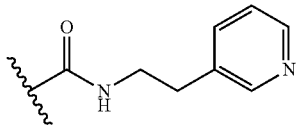 [SMILES: *C(=O)NCCc1cccnc1]
| Ex | R¹ | R³ | R⁸ 6 | R⁸ 5 | R⁸ 4 |
|---|---|---|---|---|---|
| 94 | OCF₃ | H | H | CONH₂ | H |
| 95 | CN | H | H | H | 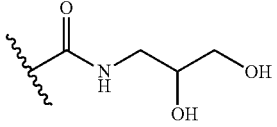 [SMILES: *C(=O)NCC(O)CO] |
| 96 | CN | H | H | H | 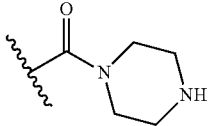 [SMILES: *C(=O)N1CCNCC1] |
| 97 | CN | H | H | H | 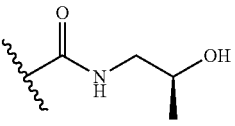 [SMILES: *C(=O)NC[C@H](C)O] |
| 98 | CN | H | CONH₂ | H | H |
| 99 | CN | H | H | 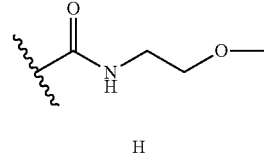 | H |
| 100 | CN | H | H | H | 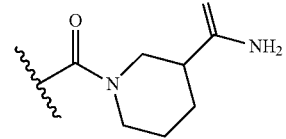 |
| 101 | CN | H | H |  | H |

TABLE 1-continued

| Ex | R¹ | R³ | R⁸ 6 | R⁸ 5 | R⁸ 4 |
|---|---|---|---|---|---|
| 102 | CN | H | H | ⸺C(O)NH-CH(CH₃)-C(O)NH₂ | H |
| 103 | CN | H | H | H | ⸺C(O)-N(pyrrolidin-3-ol) |
| 104 | CN | H | ⸺C(O)-N(azetidine) | H | H |
| 105 | CN | H | H | H | ⸺C(O)NH-C(CH₃)₂-CH₂OH |
| 106 | CN | H | H | ⸺C(O)NH-CH₂CH₂-N(CH₃)₂ | H |
| 107 | CN | H | H | H | ⸺C(O)NH-CH₂CH₂-C(O)NH₂ |

TABLE 1-continued
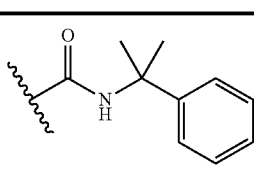
| Ex | R¹ | R³ | R⁸ 6 | R⁸ 5 | R⁸ 4 |
|---|---|---|---|---|---|
| 108 | CN | H | H | H | 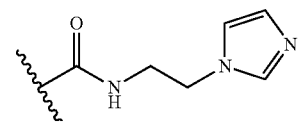 [SMILES: *C(=O)NCCn1ccnc1] |
| 109 | CN | H | H | 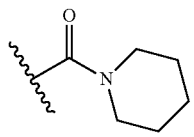 [SMILES: *C(=O)N1CCCCC1] | H |
| 110 | CN | H | H | H | 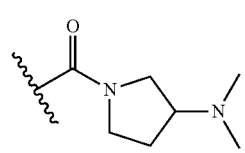 [SMILES: *C(=O)N1CCC(N(C)C)C1] |
| 111 | CN | H | 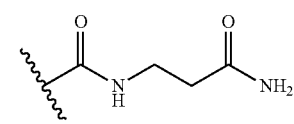 [SMILES: *C(=O)NCCC(N)=O] | H | H |
| 112 | CN | H | H | 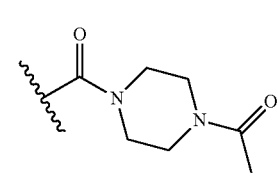 [SMILES: *C(=O)N1CCN(C(C)=O)CC1] | H |
| 113 | CN | H | H | H |  |

TABLE 1-continued

[Structure diagram shown]

| Ex | R¹ | R³ | R⁸ 6 | R⁸ 5 | R⁸ 4 |
|---|---|---|---|---|---|
| 114 | CN | H | H | H | [acetamido-N-cyclobutyl group] |
| 115 | CN | H | H | H | [prolinamide acyl group] |
| 116 | CN | H | H | [1-acyl-3-(N-methylacetamido)pyrrolidine] | H |
| 117 | CN | H | H | [N-(2-hydroxy-2-methylpropyl)acetamido] | H |
| 118 | CN | H | [N-((S)-1-phenylethyl)acetamido] | H | H |
| 119 | CN | H | H | [1-acylpyrrolidine] | H |

TABLE 1-continued

| Ex | R¹ | R³ | R⁸ 6 | R⁸ 5 | R⁸ 4 |
|---|---|---|---|---|---|
| 120 | CN | H | H | H | ⟿C(O)NH-CH(CH₃)-CH₂OH |
| 121 | CN | H | H | ⟿C(O)NH-CH₂CH₂-NHC(O)CH₃ | H |
| 122 | CN | H | H | H | ⟿C(O)-cyclopentyl-C(O)NH₂ |
| 123 | CN | H | ⟿C(O)NH-cyclopropyl | H | H |
| 124 | CN | H | H | CONMe₂ | H |
| 125 | CN | H | ⟿C(O)-N(piperidine-2-CH₂OH) | H | H |
| 126 | CN | H | H | ⟿C(O)NH-cyclopropyl | H |

TABLE 1-continued
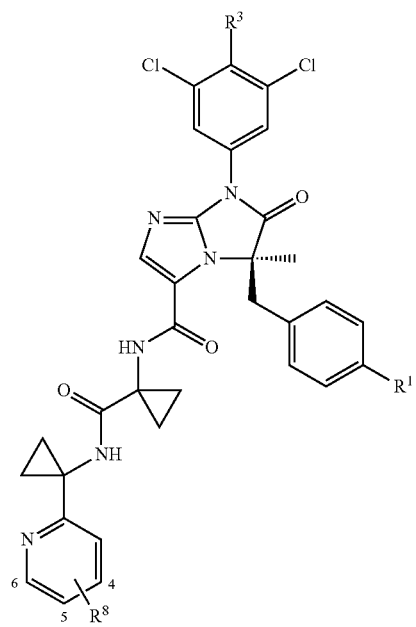
| Ex | R$^1$ | R$^3$ | 6 | R$^8$ 5 | 4 |
|---|---|---|---|---|---|
| 127 | CN | H | ⸺C(O)NHCH$_2$C(O)NH$_2$ | H | H |
| 128 | CN | H | H | ⸺C(O)NHCH$_2$CH(OH)CH$_3$ | H |
| 129 | CN | H | H | H | ⸺C(O)NHCH(CH$_2$OH)$_2$ |
| 130 | CN | H | H | ⸺C(O)-(3-hydroxypyrrolidin-1-yl) | H |
| 131 | CN | H | H | H | ⸺C(O)NHCH$_2$COOH |
| 132 | CN | H | H | H | ⸺C(O)NHCH$_2$CH$_2$NHC(O)CH$_3$ |

TABLE 1-continued
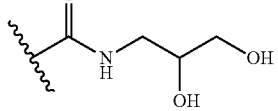
| Ex | R¹ | R³ | R⁸ 6 | R⁸ 5 | R⁸ 4 |
|---|---|---|---|---|---|
| 133 | CN | H | H | 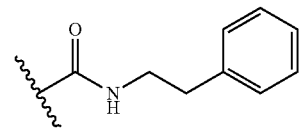 [SMILES: *C(=O)NCCc1ccccc1] | H |
| 134 | CN | H | H | 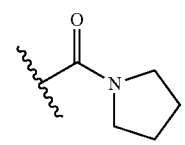 | H |
| 135 | CN | H | H | H | 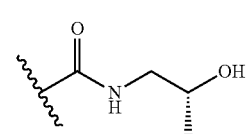 |
| 136 | CN | H | H | H | 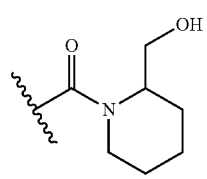 [SMILES: *C(=O)N1CCCCC1CO] |
| 137 | CN | H | H | 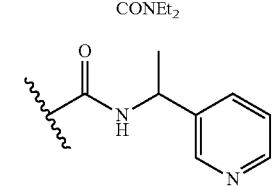 | H |
| 138 | CN | H | H | H | CONEt₂ |
| 139 | CN | H | H | H |  |

TABLE 1-continued

| Ex | R¹ | R³ | R⁸ 6 | R⁸ 5 | R⁸ 4 |
|---|---|---|---|---|---|
| 140 | CN | H | H | CONHMe | H |
| 141 | CN | H | H | *-C(O)NH-CH(CH₃)-CH₂OH* | H |
| 142 | CN | H | H | H | *-C(O)NH-CH₂-cyclopropyl* |
| 143 | CN | H | *-C(O)-(3-hydroxypyrrolidin-1-yl)* | H | H |
| 144 | CN | H | H | H | *-C(O)NH-CH₂CH₂-(4-pyridyl)* |
| 145 | CN | H | *-C(O)-morpholin-4-yl* | H | H |
| 146 | CN | H | H | H | *-C(O)NH-CH₂-CH(OH)-CH₃* |

TABLE 1-continued
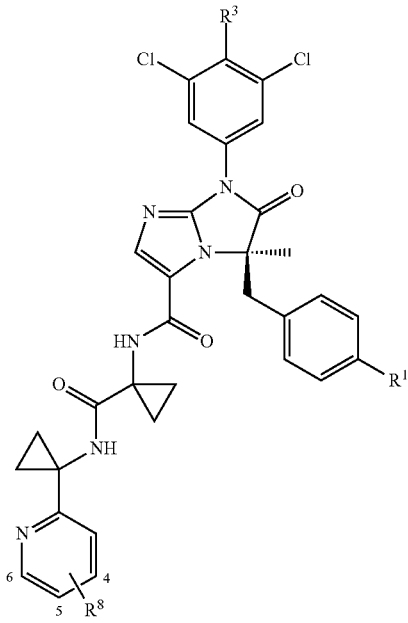
| Ex | R¹ | R³ | R⁸ 6 | R⁸ 5 | R⁸ 4 |
|---|---|---|---|---|---|
| 147 | CN | H | H | 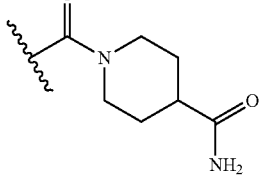 | H |
| 148 | CN | H | H | CONH$_2$ | H |
| 149 | CN | H | H | H | 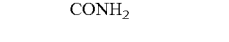 |
| 150 | CN | H | 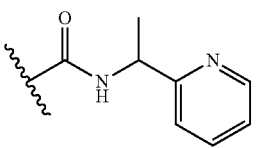 [SMILES: *C(=O)NC(C)c1ccccn1] | H | H |
| 151 | CN | H | 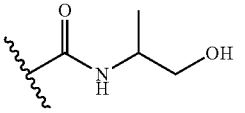 [SMILES: *C(=O)NC(C)CO] | H | H |
| 152 | CN | H | H | 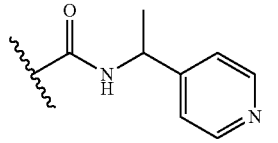 [SMILES: *C(=O)NC(C)c1ccncc1] | H |

TABLE 1-continued
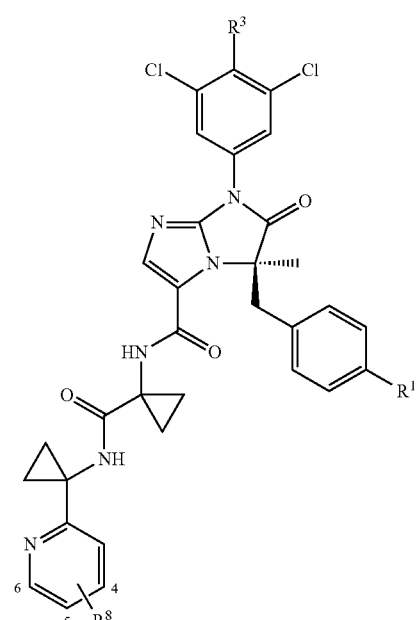
| Ex | R¹ | R³ | R⁸ 6 | R⁸ 5 | R⁸ 4 |
|---|---|---|---|---|---|
| 153 | CN | H | H | 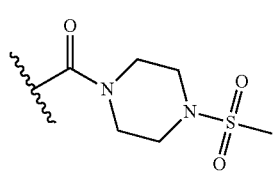 [SMILES: *C(=O)N1CCN(S(C)(=O)=O)CC1] | H |
| 154 | CN | H | H | 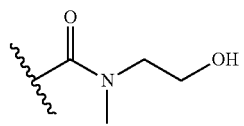 [SMILES: *C(=O)N(C)CCO] | H |
| 155 | CN | H | H | 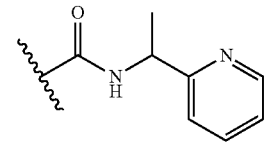 [SMILES: *C(=O)NC(C)c1ccccn1] | H |
| 156 | CN | H | H | H | 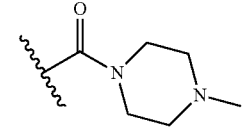 [SMILES: *C(=O)N1CCN(C)CC1] |
| 157 | CN | H | 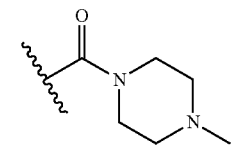 [SMILES: *C(=O)N1CCN(C)CC1] | H | H |

TABLE 1-continued
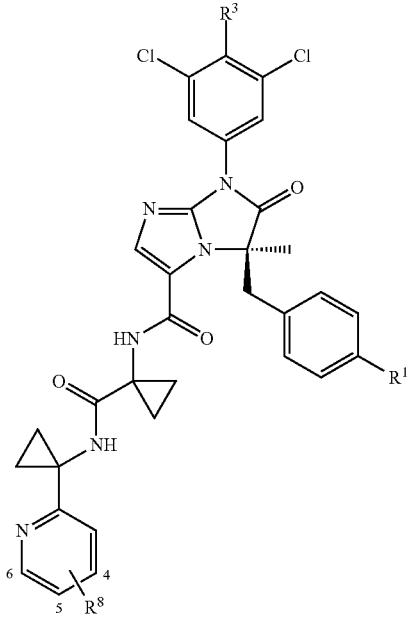
| Ex | R¹ | R³ | R⁸ 6 | R⁸ 5 | R⁸ 4 |
|---|---|---|---|---|---|
| 158 | CN | H | H | 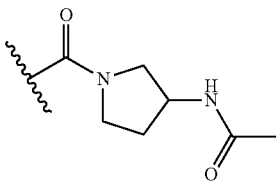 [SMILES: *C(=O)N1CCC(NC(C)=O)C1] | H |
| 159 | CN | H | H | H | 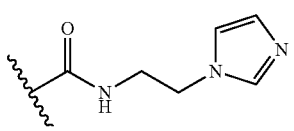 [SMILES: *C(=O)NCCn1ccnc1] |
| 160 | CN | H | H | 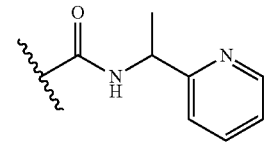 [SMILES: *C(=O)NC(C)c1ccccn1] | H |
| 161 | CN | H | 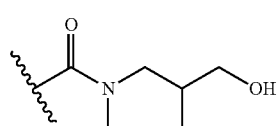 | H | H |
| 162 | CN | H | 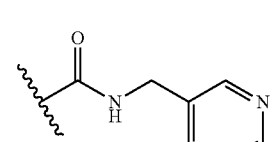 | H | H |

TABLE 1-continued
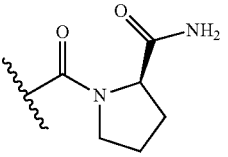 [SMILES: *C(=O)N1CCC[C@@H]1C(N)=O]
| Ex | R¹ | R³ | 6 | R⁸ 5 | 4 |
|---|---|---|---|---|---|
| 163 | CN | H | H | 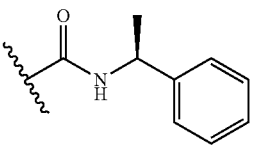 | H |
| 164 | CN | F | H | CONH₂ | H |
| 165 | CN | H | 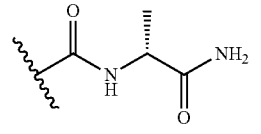 [SMILES: *C(=O)N[C@H](C)C(N)=O] | H | H |
| 166 | CN | H | H | H | 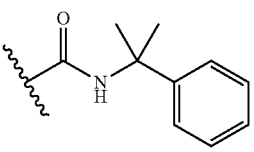 [SMILES: *C(=O)NC(C)(C)c1ccccc1] |
| 167 | CN | H | 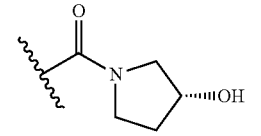 [SMILES: *C(=O)N1CC[C@@H](O)C1] | H | H |
| 168 | CN | H | H | H |  |

TABLE 1-continued

[Structure shown at top of table: a dichlorophenyl group with R³ substituent connected to an imidazo-fused bicyclic core bearing a methyl group and a 4-R¹-benzyl group, with a carboxamide linker to a cyclopropane bearing another carboxamide to a cyclopropyl-pyridinyl (with R⁸ at positions 4, 5, 6) group]

| | | | R⁸ | | |
|---|---|---|---|---|---|
| Ex | R¹ | R³ | 6 | 5 | 4 |
| 169 | CN | H | H | ![structure: -C(O)NH-CH₂CH₂-(4-pyridyl)] | H |
| 170 | CN | H | ![structure: -C(O)-N(piperidine-4-C(O)NH₂)] | H | H |
| 171 | CN | H | H | ![structure: -C(O)-N(piperazine-N-C(O)CH₃)] | H And |
| 172 | CN | H | H | H | ![structure: -C(O)NH-CH₂-C(O)NH₂] | or a pharmaceutically acceptable salt thereof.

5. A compound according to claim 4, selected from compounds 3, 4, 6, 13, 14, 17, 19, 21, 27, 29, 31, 35, 36, 41, 42, 44, 46, 49, 50, 52, 53, 55, 59, 60, 62, 66, 68, 69, 71-73, 77-79, 81, 82, 86-88, 90, 91, 94-96, 99-102, 105, 107, 109, 112, 114, 117, 120, 121, 126, 128, 129, 131-133, 136, 139-142, 144, 146-149, 154, 155, 159, 160, 163, 164, 166 and 172, or a pharmaceutically acceptable salt thereof.

6. A pharmaceutical composition comprising a compound according to claim 1, or a pharmaceutically acceptable salt thereof, and at least one pharmaceutically acceptable carrier or adjuvant.

7. A method for treating adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, necrotizing enterocolitis or granulocyte transfusion associated syndrome, psoriasis, organ/tissue transplant rejection, graft vs. host reaction, Raynaud's syndrome, autoimmune thyroiditis, dermatitis, multiple sclerosis, rheumatoid arthritis, insulin-dependent diabetes mellitus, uveitis, inflammatory bowel disease, Crohn's disease, ulcerative colitis, systemic lupus erythematosus or asthma in a patient comprising adminstering to said patient a therapeutically effective amount of a compound according to claim 1, or a pharmaceutically acceptable salt thereof.

8. A method according to claim 7, where the condition to be treated is multiple sclerosis.

9. A method according to claim 7, where the condition to be treated is psoriasis.

10. A method according to claim 7, where the condition to be treated is organ/tissue transplant rejection.

11. A method according to claim 7, where the condition to be treated is graft vs. host reaction.

12. A method according to claim 7, where the condition to be treated is systemic lupus erythematosus.

\* \* \* \* \*